(12) United States Patent
Smith

(10) Patent No.: US 7,940,937 B2
(45) Date of Patent: *May 10, 2011

(54) TRANSDUCER FOR SENSING BODY SOUNDS

(76) Inventor: Clive Smith, Centennial, CO (US)

( * ) Notice: Subject to any disclaimer, the term of this patent is extended or adjusted under 35 U.S.C. 154(b) by 1913 days.

This patent is subject to a terminal disclaimer.

(21) Appl. No.: 10/747,863

(22) Filed: Dec. 23, 2003

(65) Prior Publication Data

US 2004/0228494 A1    Nov. 18, 2004

Related U.S. Application Data

(63) Continuation-in-part of application No. 10/730,750, filed on Dec. 8, 2003, now abandoned, which is a continuation of application No. 10/328,768, filed on Dec. 23, 2002, now Pat. No. 6,661,897, which is a continuation-in-part of application No. 09/431,717, filed on Oct. 28, 1999, now Pat. No. 6,498,854.

(51) Int. Cl.
*A61B 7/04* (2006.01)

(52) U.S. Cl. ......................................................... 381/67

(58) Field of Classification Search .................... 381/67; 600/528–529
See application file for complete search history.

(56) References Cited

U.S. PATENT DOCUMENTS

| | | | | |
|---|---|---|---|---|
| 4,723,295 A | * | 2/1988 | Kosaka et al. | 381/94.5 |
| 4,765,321 A | * | 8/1988 | Mohri | 600/528 |
| 4,986,276 A | * | 1/1991 | Wright | 600/454 |
| 5,006,952 A | * | 4/1991 | Thomas | 361/283.2 |
| 5,492,129 A | * | 2/1996 | Greenberger | 600/528 |
| 5,687,246 A | * | 11/1997 | Lancon | 381/386 |
| 5,774,563 A | * | 6/1998 | DesLauriers et al. | 381/67 |
| 5,909,495 A | * | 6/1999 | Andrea | 381/67 |
| 5,932,849 A | * | 8/1999 | Dieken | 181/131 |
| 5,987,146 A | * | 11/1999 | Pluvinage et al. | 381/328 |
| 6,005,951 A | * | 12/1999 | Grasfield et al. | 381/67 |
| 6,028,942 A | * | 2/2000 | Greenberger | 381/67 |

* cited by examiner

*Primary Examiner* — Vivian Chin
*Assistant Examiner* — George Monikang
(74) *Attorney, Agent, or Firm* — Colin P. Abrahams

(57) ABSTRACT

An acoustic-to-electrical transducer for sensing body sounds is disclosed. The transducer comprises a diaphragm that can be placed in direct contact with a body, whereby the diaphragm motion directly affects an electromagnetic sensing signal, which is then converted to an electrical signal representation of the diaphragm motion. Such sensing means allows the diaphragm to move freely without mechanical coupling to a secondary transducer, while providing a direct and efficient acoustic to electrical conversion means. The transducer further provides a means for using static diaphragm pressure to control gain and frequency characteristics of the electrical signal. The transducer provides methods for ambient noise reduction or cancellation, as well as means for simulating sound detection for applications such as medical education and testing. The sensor, circuitry, manufacturing methods and improvements are disclosed.

3 Claims, 18 Drawing Sheets

(A)  (B)  (C)  (D)

(A)  (B)  (C)

TRANSDUCER FOR SENSING BODY SOUNDS

CROSS REFERENCE TO RELATED APPLICATIONS

This application is a continuation-in-part of U.S. patent application Ser. No. 10/730,750 filed Dec. 8, 2003, which is a continuation of U.S. patent application Ser. No. 10/328,768 filed Dec. 23, 2002, now U.S. Pat. No. 6,661,897, which is a continuation in part of U.S. patent application Ser. No. 09/431,717 filed Oct. 28, 1999, now U.S. Pat. No. 6,498,854, all of which are incorporated herein by reference in their entirety.

FIELD OF THE INVENTION

The present invention relates to sensing body sounds, and more specifically, to acoustic-to-electrical transducers used for sensing body sounds, especially in stethoscopes.

BACKGROUND OF THE INVENTION

Stethoscopes are widely used by health professionals to aid in the detection of body sounds. The procedures for listening to and analyzing body sounds, called auscultation, is often difficult to learn due to the typically low sound volume produced by an acoustic stethoscope. Electronic stethoscopes have been developed which amplify the faint sounds from the body. However, such devices suffer from distortion and ambient noise pickup. The distortion and noise are largely due to the performance of the acoustic-to-electrical transducers, which differ in operation from the mechanical diaphragms used in acoustic stethoscopes.

Acoustic stethoscopes have been the reference by which stethoscope sound quality has been measured. Acoustic stethoscopes convert the movement of the stethoscope diaphragm into air pressure, which is directly transferred via tubing to the listener's ears. The listener therefore hears the direct vibration of the diaphragm via air tubes.

Existing electrical stethoscope transducers are typically one of three types: (1) microphones mounted behind the stethoscope diaphragm, or (2) piezo-electric sensors mounted on, or physically connected to, the diaphragm, or (3) other sensors which operate on the basis of electro-mechanical sensing of vibration via a sensing mechanism in mechanical contact with the diaphragm placed against the body Microphones mounted behind the stethoscope diaphragm pick up the sound pressure created by the stethoscope diaphragm, and convert it to electrical signals. The microphone itself has a diaphragm, and thus the acoustic transmission path comprises stethoscope diaphragm, air inside the stethoscope housing, and finally microphone diaphragm. The existence of two diaphragms, and the intervening air path, result in excess ambient noise pickup by the microphone, as well as inefficient acoustic energy transfer. Various inventions have been disclosed to counteract this fundamentally inferior sensing technique, such as adaptive noise canceling, and various mechanical isolation mountings for the microphone. However, these methods are often just compensations for the fundamental inadequacies of the acoustic-to-electrical transducers.

The piezo-electric sensors operate on a somewhat different principle than merely sensing diaphragm sound pressure. Piezo-electric sensors produce electrical energy by deformation of a crystal substance. In one case, the diaphragm motion deforms a piezoelectric sensor crystal which is mechanically coupled to the stethoscope diaphragm, and an electrical signal results. The problem with this sensor is that the conversion mechanism produces signal distortion compared with sensing the pure motion of the diaphragm. The resulting sound is thus somewhat different in tone, and distorted compared with an acoustic stethoscope.

Other sensors are designed to transfer mechanical movement of the diaphragm, or other surface in contact with the body, via some fluid or physical coupling to an electromechanical sensing element. The problem with such sensors is that they restrict the mechanical movement of the diaphragm by imposing a mechanical load on the diaphragm. Acoustic stethoscopes have diaphragms that are constrained at the edges or circumference, but do not have any constraints within their surface area, other than the inherent elasticity imposed by the diaphragm material itself. Thus placing sensors in contact with the diaphragm restrict its movement and change its acoustic properties and hence the sounds quality.

Capacitive acoustic sensors have been disclosed and are in common use in high performance microphones and hydrophones. A capacitive microphone utilizes the variable capacitance produced by a vibrating capacitive plate to perform acoustic-to-electrical conversion. Dynamic microphones that operate on the principle of a changing magnetic field are well-known. These devices typically operate by having a coil move through a static magnetic field, thereby inducing a current in the coil. Optical microphones have been disclosed, which operate on the principle that a reflected light beam is modified by the movement of a diaphragm.

A capacitive, magnetic or optical microphone placed behind a stethoscope diaphragm would suffer from the same ambient noise and energy transfer problems that occur with any other microphone mounted behind a stethoscope diaphragm. A unique aspect of the present invention is that the stethoscope diaphragm is the only diaphragm in the structure, whereas existing microphone-based solutions comprise a stethoscope diaphragm plus a microphone diaphragm, resulting in the inefficient noise-prone methods described previously.

The present invention provides both direct sensing of the diaphragm movement, with the diaphragm making direct contact with the body, while at the same time avoids any change in acoustic characteristics of the diaphragm compared with that of an acoustic stethoscope, since the sensing means does not mechanically load the diaphragm. This results in efficient energy transfer, and hence reduced noise, with acoustic characteristics that are faithful to that of an acoustic stethoscope diaphragm. The present invention discloses three basic embodiments: (a) A capacitive sensor, (b) a magnetic sensor, and (c) an optical sensor.

Body sound transducers and stethoscopes in particular have been plagued by pickup of ambient noise in addition to body sounds. The chestpieces of acoustic and electronic stethoscopes must typically be sealed so that air does not leak to the outside atmosphere. Thus stethoscope chestpieces have closed cavities, which result in standing waves and acoustic resonance within the cavity. Such acoustics tend to exacerbate the effects of ambient noise which reverberates in the chestpiece. The present invention provides openings in the transducer to mitigate this problem. Diaphragm dynamics and tension also affect transducer response and the present invention provides a means to make such dynamics adjustable.

Noise canceling methods have also been applied to body sound detectors and capacitive transducers in general. Noise canceling must be applied to signals received from the transducer. The present invention provides for the cancellation of noise signals at the capacitive transducer electrodes prior to electronic amplification.

Learning auscultation has always been a difficult process. Body sound simulators have been developed, such as "Harvey", which have acoustic and mechanical sound sources within a manikin so that students can learn sounds and the locations at which they are typically found. The present invention provides for the simple adaptation of the body sound transducers herein and the capacitive transducer in particular, to be used in conjunction with a body sound simulator that has no moving parts, and does not require acoustic signal generation which is subject to dispersion and signal loss within the manikin body. Such simulation techniques can be applied to other applications in education and entertainment wherein electrodes placed on a body or object produce signals which can be detected by minimally-modified body sound transducers.

SUMMARY OF THE INVENTION

According to one aspect of the invention, there is provided a acoustic-to-electrical transducer for detecting body sounds, the transducer comprising (a) a capacitive to electrical conversion means, or (b) a magnetic to electrical conversion means, or (c) an optical (light) to electrical conversion means.

The capacitive to electrical conversion means comprises: a diaphragm having an electrically conductive surface, the diaphragm being mounted in a housing such that the diaphragm can contact a body for body sound detection; a conductive plate substantially parallel to the diaphragm, mounted within the housing, the conductive plate being positioned behind and spaced from the diaphragm to allow diaphragm motion, the diaphragm and conductive plate being connected in the form of an electrical capacitance to electrical circuitry; and a capacitance-to-electrical signal conversion means to convert capacitance changes to electrical signals.

The magnetic to electrical conversion means comprises a diaphragm that is placed against the body, the diaphragm having magnetic elements such as a permanent magnetic surface or electrically-induced magnetic field due to a wire or printed-circuit coil, so that a magnetic field is set up that is subject to change by motion of the diaphragm. The conversion means additionally comprises a magnetic field sensing means to convert the magnetic field changes to an electrical signal. Thus diaphragm motion affects the magnetic field, the magnetic field changes an electrical signal, and acoustic to electrical conversion is achieved.

The optical to electrical conversion means comprises a diaphragm placed against the body, with a light path that can be modified by motion of the diaphragm. A light source transmits visible or infrared light to the diaphragm. The diaphragm reflects the light, which is then detected by an optical detector, and changes in the reflected light signal due to diaphragm motion are then converted to an electrical signal. Another embodiment of the optical method is transmissive, with the light beam passing through an optical element that moves with the diaphragm, the motion of the optical element causing changes in the light beam received by the optical detector.

The present invention provides an acoustic-to-electrical transducer means for the detection of body sounds, such as for use in a stethoscope. The term "body" in this specification may include living or inanimate bodies. Living bodies may include humans and animals, while inanimate bodies may include, by example only, buildings, machinery, containers, conduits, vibrating objects and the like. The sensor detects stethoscope diaphragm movement directly, converting the diaphragm movement to an electrical signal which is a measure of the diaphragm motion. Further amplification or processing of the electrical signal facilitates the production of an amplified sound with characteristics closely resembling the acoustic stethoscope sound, but with increased amplification, while maintaining low distortion. This is a significant improvement over the more indirect diaphragm sound sensing produced by the existing microphonic or piezoelectric methods described above. Since the diaphragm motion is sensed directly, the sensor is less sensitive to outside noise than the other methods described, and the signal is a more accurate measure of the diaphragm movement. In the case of the acoustic stethoscope, diaphragm movement produces the acoustic pressure waves sensed by the listener's ears, and in the case of the present invention, that same diaphragm movement produces the electrical signal in a direct manner, the signal eventually being used to drive an acoustic output transducer such as headphones, to set up the same acoustic pressure waves impinging on the listener's ears.

A fundamental advantage of the present invention is that diaphragm movement is not impeded by the acoustic-to-electrical conversion means, since there is a spacing between the diaphragm and other transducer elements. Therefore, the acoustic characteristics of the diaphragm are maintained, and the sound more closely resembles an acoustic stethoscope sound, which is familiar to the current user base of doctors, nurses and others. This is a unique aspect of this invention, in that other acoustic sensors do not require the amount of diaphragm motion required for a contact-type sensing device such as a stethoscope. Thus while other applications require only tens of microns of spacing, and the diaphragms typically move only a few microns when in use, this invention allows for movement of the diaphragm of more than 0.1 mm. Depending on the stiffness of the diaphragm, pressure against the body can result in 0.1 mm, 0.2 mm, 0.5 mm or even 1 mm of diaphragm displacement due to pressure.

The present invention discloses three sensing methods.

The first embodiment utilizes a capacitive sensing method. Capacitive acoustic sensors have been disclosed and are in common use in high performance microphones and hydrophones. However, the present invention uses the stethoscope diaphragm itself as one plate of the capacitive sensor which touches the body surface directly. This method of direct contact capacitive sensing of body sounds as described, is unique.

The sensor comprises a movable diaphragm with a conductive plane or surface, and a co-planar conductive surface (electrode or plate) placed behind the diaphragm, with a space or electrolyte between the two elements. The diaphragm's conductive surface, in conjunction with the second conductive plate, form a capacitor. Movement of the diaphragm due to motion or sound pressure modulates the distance between the diaphragm and plate, producing a change in capacitance. One unique aspect of the invention lies in the fact that the stethoscope diaphragm forms one plate of the capacitor.

A feature of the invention is that the diaphragm, being the same element that makes contact with the body, is primarily sensitive to sounds emanating from the body, rather than sound transmitted through the air from ambient noise. By making contact with the body, the acoustic impedance of the sensor becomes matched to that of the body, rather than the surrounding air. Therefore, the capacitance change due to diaphragm motion is primarily due to body sounds, rather than overall ambient noise.

While a number of means are available for converting the capacitance variation to an electrical signal, the preferred embodiment performs this conversion by charging the capacitance formed by the diaphragm-plate combination to a high DC voltage, via a high resistance. This produces a somewhat constant charge on the capacitor. Movement of the diaphragm then produces a variation in the capacitance. If the capacitor charge is fixed, and the capacitance varies with time, a small AC variation in capacitance voltage is produced. This is sensed by a high-impedance amplifier, which is designed to detect the AC changes in capacitance voltage while avoiding rapid discharge of the capacitor.

A second method for detecting capacitance change is to employ the same diaphragm-plate capacitance in a high-frequency resonant or oscillation circuit, and detect changes in oscillation frequency produced by changes in the time constant of the capacitive circuit.

A third method of constructing a capacitive sensor, and sensing capacitance variation is via the use of an electret technique. This method requires that one or both of the plates of the capacitor formed by the diaphragm-plate be coated with a permanently charged material, such as an electret material, to create a permanent electric field between the plates. Since the plate, or plates, have a permanent electric field between them, the production of a high DC charge voltage is obviated, and voltage changes can be produced due to movement without the need for a DC charge voltage produced via a circuit.

A fourth method of constructing a capacitive sensor is to build the capacitive elements on a semiconductor substrate. In this case, the diaphragm contacts the body, there is a spacing for diaphragm motion, and the rear capacitive plate comprises the aluminum, copper or polysilicon conductive material as one of the layers of a semiconductor process. The fundamental principle of the invention still applies in that a diaphragm in contact with a body forms a movable capacitive electrode.

Any method of detecting capacitance change and converting such change to an electrical signal is encompassed by this invention. This invention therefore covers all such methods for detecting capacitance changes due to diaphragm motion.

It should be noted that while the preferred embodiment comprises a fixed plate behind the diaphragm, the invention includes methods whereby both plates are flexible and form a capacitance. In such a case, the basic principle applies whereby the capacitance varies due to sound pressure from the body, but the second plate is not necessarily rigid.

In the preferred embodiment, the fixed plate is mounted behind the diaphragm. In order to ensure acoustic isolation from external sounds, the fixed plate should preferably be mounted through a means which acoustically isolates it from the housing, or uses a means intended to prevent the fixed plate from vibrating. This is an important improvement which enhances noise isolation.

A variation of the basic principle of operation is to create two capacitors, by having the conductive diaphragm as described, with a conductive plate behind the diaphragm forming one capacitor, and a third plate behind the second, forming a second capacitor. The diaphragm and second plates are charged, while the third, rear plate is connected to an amplifier circuit. This two-capacitor method operates on essentially the same principle, whereby voltage across a charged capacitor varies in response to distance between plates, one plate being formed by the diaphragm. A further feature of the invention, is the method for constructing and producing the diaphragm. The diaphragm material must be flexible, and conduct electricity, in order to perform as a variable capacitor plate sensitive to sound pressure. This electrically conductive surface is preferably, but not necessarily, electrically insulated from the surface of the diaphragm that touches the body, for both safety and interference-prevention purposes.

A further feature of the preferred embodiment is the capacitive sensing circuitry connected to the diaphragm-plate capacitor. In the preferred embodiment, the circuit comprises two critical elements: (1) a high voltage DC bias generator with very high impedance, and (2) an AC amplifier with very high impedance to sense AC voltage changes without discharging the capacitor.

The invention also includes methods for signal amplitude control, DC charge voltage control to preserve battery power, and construction and manufacture of the capacitive sensor.

The first magnetic sensor embodiment of the invention comprises a diaphragm with permanently magnetized material adhered to or integral to the diaphragm, such that diaphragm movement results in changes in the magnetic field in the space behind the diaphragm. A magnetic field sensor is than placed at a distance from the diaphragm, but sufficiently close to detect changes in magnetic field due to diaphragm motion. The field sensor then converts magnetic field changes to an electrical signal. The diaphragm is housed such that it can be placed in direct contact with the body for body sound detection.

In another magnetic sensor embodiment, the diaphragm can be placed against the body, and has an electrical conductor on the rear side of the diaphragm such as a wire coil or printed circuit attached to the diaphragm or printed onto the diaphragm. A current in the coil sets up a magnetic field, or senses changes in a magnetic field produced by another coil or permanent magnet that is fixed behind the moving diaphragm. The diaphragm coil, or another magnetic field sensing means, converts changes in the magnetic field due to diaphragm motion to an electrical signal. Thus the coil can either produced the magnetic field and another circuit perform field detection, or the field can be produced by a separate magnet or circuit, and the diaphragm coil can perform field detection.

An optical sensor embodiment of the invention comprises a diaphragm which has optical elements, such as a reflective or transmissive plane integral to the diaphragm structure. A light transmitter, such as a laser or visible or infrared emitter is placed behind the diaphragm. A light sensor such as a photodiode or phototransistor is also placed behind the diaphragm such that it can detect the reflected light signal being modified by diaphragm motion. The sensor then converts the changing light signal to an electrical signal.

In one embodiment of the optical diaphragm structure, light from the emitter strikes the rear diaphragm surface. The surface or an underlying layer has a reflective pattern that produces either a pulsating or variable analog reflection signal that is then sensed by the optical detector and converted to an electrical signal.

In a second embodiment of the optical transducer, an optical structure such as a film is placed normal to the diaphragm plane, on the rear side of the diaphragm. The emitter and detector are placed such that the optical structure is within the light path between emitter and detector. The light path might be transmissive or reflective. In either case, diaphragm motion produces motion in the optical structure attached to the diaphragm, and the light signal is modified by mechanical movement of the diaphragm. This light signal is then converted to an electrical signal.

In all of the above embodiments, and others suggested by the invention, the diaphragm is physically separated from the conversion mechanism so that diaphragm movement is unimpeded. At the same time, the sensing means directly detects diaphragm motion in the form of a changing electric field, magnetic field, or optical signal. Thus the advantages of direct diaphragm sensing are achieved without the mechanical resistance of a mechanical sensor compromising acoustic characteristics of the diaphragm.

Improvements in the present invention provide for mitigation of ambient noise effects. Stethoscopes and body sound transducers in general are affected by ambient noise being picked up by the transducer. The present invention provides for a transducer housing that can be opened to reduce or eliminate standing waves and resonant effects that tend to create ambient noise reverberations in closed body sound transducer housings. This is a novel modification of existing transducer housings since a sealed cavity placed against the body is essential to the operation of pneumatic/acoustic and microphone-based electronic stethoscopes. Opening the housing allows more ambient noise into the transducer housing yet improves the perceived sound quality. This is a surprising and counterintuitive result. Since the present invention does not rely on a sealed cavity, this change in cavity acoustics can be exploited to improve response to ambient noise.

The dynamics of the diaphragm are critical to the performance of the body sound detector. The present invention provides for an adjustable diaphragm dynamic so that users can set the dynamics of the diaphragm to a preferred response characteristic.

Another noise mitigation technique provided in this invention is the use of noise canceling at the front-end input of the capacitive transducer. An anti-noise signal drives the electrode(s) of the capacitance used for body sound detection. This signal nulls the signal produced by displacement of the conductive diaphragm. This results in noise cancellation within the transducer capacitor itself prior to any amplification or electronic processing. This is a unique benefit of the present invention, providing for very effective noise cancellation techniques.

Capacitive transducers detect changes in electric field or voltage. In the case of vibrational transducers, this change is produced by displacement of a diaphragm and the changing space between electrodes of a capacitance. This invention provides for modification of the transducer so that the transducer can detect changes in voltage on an external electrode, when the transducer is placed in capacitive or conductive contact with said external electrode or multiple electrodes. Such external electrodes can be driven by a signal source and placed on the surface of a body or object. This scheme can be applied to the construction of educational models or manikins, or clothing that can be worn, whereby the body sound detector, modified to detect electric fields, can be used for educational or recreational purposes. Specifically, a manikin can be constructed with multiple electrodes, driven by a multi-channel signal source. A student can then place the body sound detector, preferably as part of a stethoscope, on the manikin at various sites, and hear the sound that would be emitted at that site on a patient. The sounds can be selected from a library of pathologies to simulate numerous pathologies. Similar methods can be adopted for the magnetic and optical transducers, however the capacitive method is the preferred embodiment.

Improvements in the transducer therefore include noise reduction, performance, and modification of the sensor to detect not just sound but other phenomena.

DETAILED DESCRIPTION OF THE PREFERRED EMBODIMENTS

Figure 1:
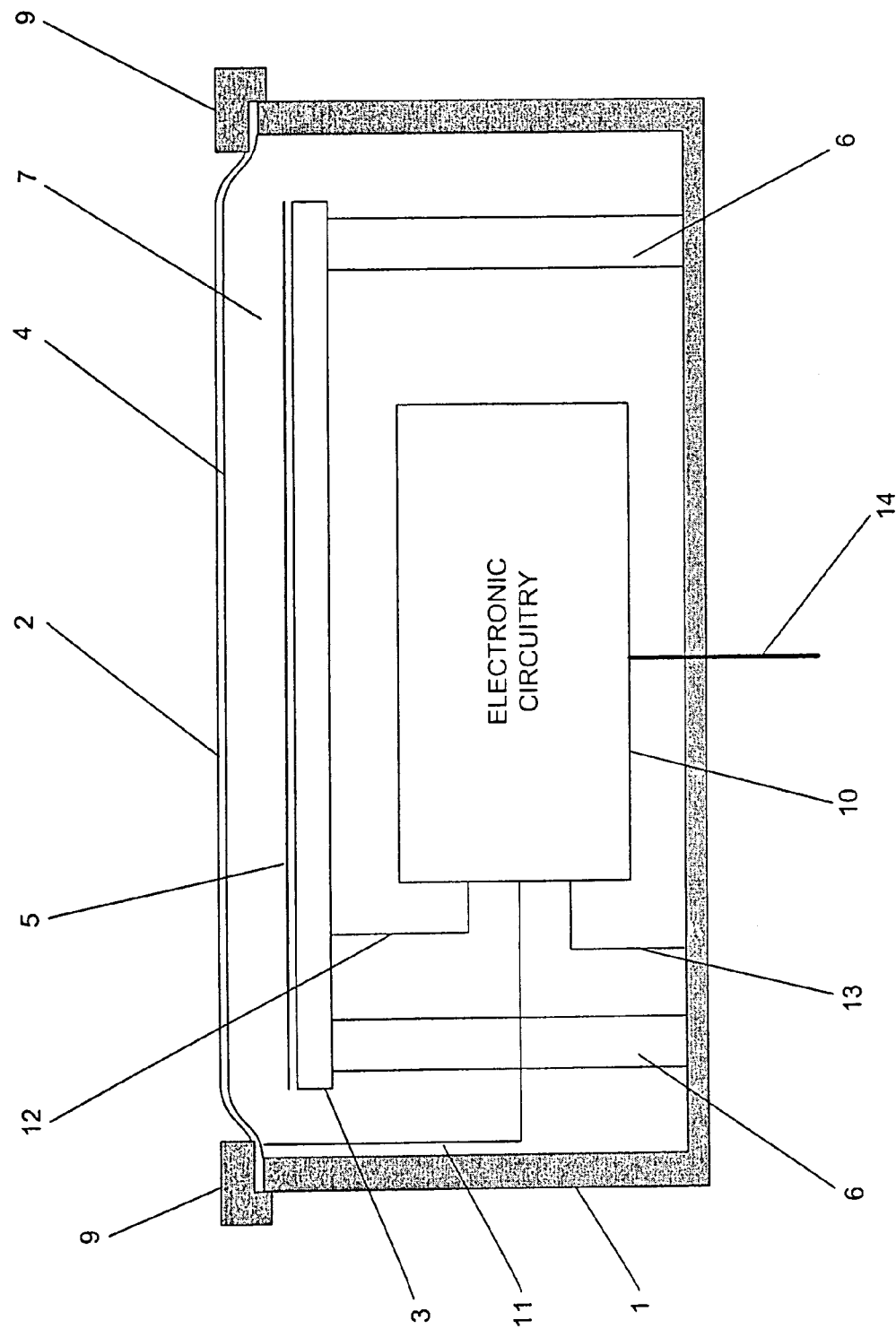
FIG. 1 shows the basic mechanical structure of the invention in one preferred embodiment.

The preferred embodiments are divided into three categories—(a) Capacitive Sensor embodiments, (b) Magnetic Sensor embodiments, and (c) Optical Sensor embodiments. These are all discussed separately below.

A fundamental aspect of the invention, covering all embodiments, is (a) that the diaphragm makes direct contact with the body for sound sensing, (b) the diaphragm is an integral part of the acoustic-to-electric transducer mechanism rather than simply transmitting sound waves via air to a second acoustic-to-electrical transducer i.e. in this invention the diaphragm motion itself is converted to an electrical signal and (c) the mechanical structure of transducer elements other than the diaphragm do not make direct contact with the diaphragm and hence the conversion means does not impede diaphragm motion or place a mechanical load on the diaphragm.

The benefit of this method is that the acoustic properties of the diaphragm are essentially the same as those of an acoustic stethoscope due to the freedom of movement of the diaphragm, and the direct conversion of diaphragm motion that ensures efficient energy conversion from acoustic to electrical energy. Further, the direct conversion method decreases or eliminates the insertion of ambient noise into the conversion process, since ambient noise usually enters the system between the diaphragm and any secondary transducer.

Another unique aspect of the invention is the operation of the diaphragm in this invention compared with diaphragms in conventional microphones. In a conventional microphone, the diaphragm does not make physical contact with any body, the sound being coupled from the source via air, or fluid in the case of a hydrophone. The diaphragm displacement is therefore very limited, typically less than 5 microns displacement. The diaphragms are therefore designed to be displaced a few microns, and the spacing of the diaphragm to other elements behind the diaphragm is typically on the order of tens of microns. In most cases, the goal of conventional microphone design is to minimize such diaphragm spacing in order to optimize performance and sensitivity. It is thus counterintuitive to (a) place a diaphragm directly against the body, (b) allow the diaphragm to withstand the large displacements produced by pressure against a body, and (c) to construct a sensor that increases, rather than decreases, the displacement capability of the diaphragm. Thus in stethoscope applications, the prior art either includes placement of a microphone (with its own diaphragm) behind the stethoscope diaphragm, ensuring that the microphone diaphragm cannot contact the body as well as making the system susceptible to noise, or a mechanical coupling is used that loads the diaphragm thereby limiting its ability to move with any substantial displacement as well as modifying the diaphragm's acoustic characteristics. This invention resolves both problems simultaneously.

In the present invention, the spacing between the diaphragm and any other element of the transducer placed behind the diaphragm typically exceeds 0.1 mm, 0.25 mm, 0.5 mm or 1 mm, subject to the stiffness and radius of the diaphragm, and the mounting means. The present invention addresses stethoscope diaphragms which are typically in excess of 25 mm diameter, although smaller diaphragms are also covered by the invention. If the diaphragm mounting means allows substantial diaphragm displacement, the spacing is increased. If the mounting is more rigid, and the diaphragm material sufficiently stiff to withstand pressure, the spacing can be reduced. In the case of an embodiment that is produced by semiconductor processing means, such that the transducer forms part of a semiconductor integrated circuit, the spacing can be made substantially smaller than 0.1 mm, since the diaphragm diameter is then significantly smaller than a conventional stethoscope diaphragm.

All embodiments of this invention include considerations of spacing and diaphragm displacement, and the numerical values defined above cover all embodiments.

Another aspect of the displacement characteristic of the diaphragm in this invention is the capability to allow static pressure from a body to change the steady-state position of the diaphragm about which vibrations occur due to sound. Thus when the diaphragm is pressed against a body for listening, the diaphragm moves from its unpressured position to a new displacement due to pressure. This is referred to as the static displacement. Then acoustic waves produce smaller dynamic displacement or vibration from sub-sonic (5 Hz-20 Hz) through audio frequency range (20 Hz to 20 KHz). In this case, most sounds of interest do not cover the entire audio range, but are limited to approximately 10 Hz to 2000 Hz. In the present invention, the static and dynamic displacements are used to control the sound characteristics of the transducer in a novel way. The static displacement influences the gain or amplitude of the transducer. The static displacement also affects the frequency response of the transducer. Thus the user can control amplitude and frequency characteristics by applying different static pressures to the diaphragm as it is pressed against the body. The prior art seeks to establish uniform amplitude and frequency characteristics for electronic transducers, so that there is no user-to-user variability. This invention exploits the inherent feedback loop that allows a user to hear the amplitude and frequency characteristics, and adjust pressure on the diaphragm to control for the optimal sound characteristics. While acoustic stethoscopes do provide for modification of sound characteristics with pressure, these effects have not been implemented in electronic stethoscope transducers. Further, the acoustic diaphragms that facilitate this effect do so by modification of the effective diameter of the diaphragm. This invention is novel in that diaphragm displacement is used as the controlling parameter, and the means for effecting this acoustic change have not been achieved with electronic transducers in this application.

This invention includes three primary embodiments of the fundamental inventive steps described above—capacitive, magnetic and optical sensing embodiments.

Capacitive embodiments are presented in FIGS. 1 to 9, Magnetic embodiments are presented in FIGS. 10 to 13, and optical embodiments are presented in FIGS. 14 to 17.

With reference to the drawings, FIG. 1 shows the basic mechanical structure of the invention in its preferred capacitive embodiment. A housing 1 contains a capacitive sensing mechanism comprising a movable flexible diaphragm 2, with electrically conductive surface 4, such surface preferable being on the inner surface, placed co-planar to an electrically conductive plate 3, with some intervening space 7 filled with air or an electrically nonconductive fluid or gaseous substance. The diaphragm 2 and plate 3 form a capacitor. Motion of the diaphragm 2 due to sound pressure varies the distance between diaphragm 2 and plate 3, thereby varying the capacitance of the diaphragm-plate capacitance, since the capacitance is inversely proportional to the distance between the diaphragm 2 and the plate 3. A unique aspect of the invention is that the stethoscope diaphragm 2 forms one plate of a capacitive sensor, whereby the motion of the diaphragm 2 varies capacitance, which then varies other circuit parameters in an electronic circuit, to generate a time-varying electrical signal measuring diaphragm motion. The diaphragm motion is then a measure of the sound being detected, and hence the invention forms an effective body sound sensor.

There are various methods for manufacturing the capacitive diaphragm. One method is to use a substrate of glass epoxy of approximately 0.125 mm to 0.635 mm thickness for the diaphragm 2. The substrate in then coated with a conductive paint via a spray painting, silkscreening or similar process, or a vapor deposition of aluminum or other metal is done. This provides the conductive plane 4. The diaphragm can then be coated with an insulation material, to provide the insulation layer 5. This invention is not limited to these methods for producing capacitive diaphragms. Alternative substrate materials include polycarbonate and mylar, as examples. It is also noted that the substrate materials suggested here are also suitable for use in the magnetic and optical embodiments disclosed in this invention. The diaphragm might also be manufactured with other coatings and layers, such as silkscreened paint with product information or other miscellaneous information, such as model numbers, brand names or advertising. Such layers do not affect the operation of the invention.

In a preferred embodiment, the diaphragm 2 is mounted to the housing 1 via an attachment means 9 which provides acoustic isolation or significant acoustic wave attenuation from the housing 1. This can be achieved by selection of a sound absorbing material for the attachment 9, and/or by shaping the diaphragm 2 such that vibration from the outside circumference of the diaphragm 2 is not coupled to the major surface area thereof. The plate 3 is mounted behind the diaphragm via mounting brackets 6, which provides acoustic isolation or attenuation from the housing in order to reduce ambient noise pickup by preventing the plate 3 from vibrating.

The diaphragm 2 is mechanically housed such that it can be placed in physical contact with a body to sense sound from the body by direct physical contact, rather than via a fluid or air medium as is typical of microphones and hydrophones. This imposes on the diaphragm 2 a preferred property that it be capable of a displacement significantly larger than that typically required for a microphone or hydrophone diaphragm, making space 7 larger than that typical of air microphones or hydrophones. In a preferred embodiment, the distance between diaphragm 2 and plate 3 typically exceeds 0.1 mm. This is a somewhat unique characteristic of this sensing application, resulting in a very low diaphragm-plate capacitance.

The displacement of diaphragm 2 that is facilitated by the spacing between diaphragm 2 and plate 3 takes the form of two displacements—a larger static displacement due to static pressure of the diaphragm against the body, and a smaller dynamic displacement due to acoustic vibration. In both cases, the capacitance is changed, and one can consider these two capacitance changes separately.

The dynamic change due to vibration is small and produces sub-sonic and audio-frequency voltage changes.

The static capacitance change due to static pressure applied to the diaphragm provides a unique aspect of this invention by changing the steady-state capacitance of the transducer in use as a function of this static pressure against the body. This static change causes the gain and the passband frequency of the transducer to change, in response to pressure, since the gain is a function of distance between diaphragm 2 and plate 3, and the passband cutoff frequency is a function of the RC time constant of the input stage of the circuit, where R is the input impedance of the amplifier 54, and C is the capacitance of the transducer. Since C is a function of capacitive spacing which is a function of static pressure, the time constant, and hence the transducer frequency response can be affected by pressure changes against the body.

A unique aspect of this invention is that the user is able to control amplification (gain) and frequency response of the transducer by adjusting the pressure applied to the diaphragm 2. Since the user can hear the sound while the invention is in use, the user becomes part of a feedback loop, in which pressure is adjusted by the user to optimize the sounds quality and amplitude according to the user's needs. This is in contrast to conventional capacitive sensors, in which the distance between plates is tightly controlled, and it is counter-intuitive that variation of static capacitance would be beneficial to the user. In most capacitive sensors, the spacing is also too small to allow for much, if any, static variation, since the goal of such devices is to allow only as much spacing as needed for dynamic changes, such as those due to vibration. It has further been assumed that gain and frequency response should also be tightly controlled parameters not subject to user interaction or control.

An alternative embodiment of the invention allows the spacing between the conductive plates of the transducer capacitance to be filled with a deformable material such as foam, or liquid. These embodiments include the characteristics disclosed above for air-filled capacitive spacing.

In a preferred embodiment of the invention, a high voltage potential is generated between the diaphragm 2 and plate 3. Using such a method, electrical insulation is required of a number of elements in the invention. A high-dielectric insulator 5, made from substances such as Mylar film produced by E.I. Du Pont, or Ultem film manufactured by General Electric, is optionally placed between the diaphragm 2 and plate 3. This reduces electronic noise caused by discharge of the capacitance across the space 7 between the diaphragm 2 and plate 3. While the insulator 5 is not essential to sensor operation, it enhances sound quality. The dielectric insulator 5 can be deposited onto the diaphragm 2, as a coating that covers the conductive plane, or it can be deposited or adhered to the plate 3. Alternatively, it can merely be placed between the diaphragm 2 and plate 3. The plate 3 is mounted via a mounting bracket 6 to the housing 1, such mounting bracket being made of a material which provides high electrical isolation, such as nylon or Teflon. This prevents trickle discharge of the plate 3. The preferred electrical insulation requirements stated above are relevant to the embodiment of the invention that requires a high voltage potential between the plate 3 and diaphragm 2. Other embodiments do not necessarily require such high quality electrical insulation, since they might rely on methods of capacitance measurement which does not require a significant DC voltage on the capacitance. An embodiment that is included in this invention comprises a diaphragm 2 that forms a capacitance with a conductive plate 3 that is part of a semiconductor integrated circuit. This plate 3 is formed from aluminum, copper or polysilicon conductive material. In this embodiment, the insulator 5 can comprise an insulation layer typical of semiconductor processes such as silicon dioxide.

The electrical connections are shown in FIG. 1, for one embodiment of the invention. An electronic circuit 10 is preferably mounted within housing 1, with connection 13 to the housing 1, connection 11 to the diaphragm conductive surface 4, and connection 12 to the plate 3. External power and signal connections are provided via connection means 14. The principle of operation of the sensor does not require that the associated circuitry be placed within housing 1. However, best performance is obtained by placing amplifier circuitry close to the sensing capacitance. In the case of a semiconductor implementation of the capacitive sensor, the electronic circuit 10 and connections can be included on one integrated circuit, forming a single structure with capacitive sensor and electrical circuitry. In this embodiment, the diaphragm 2 is still mounted such that it can make direct contact with the body for sensing.

Figure 2:
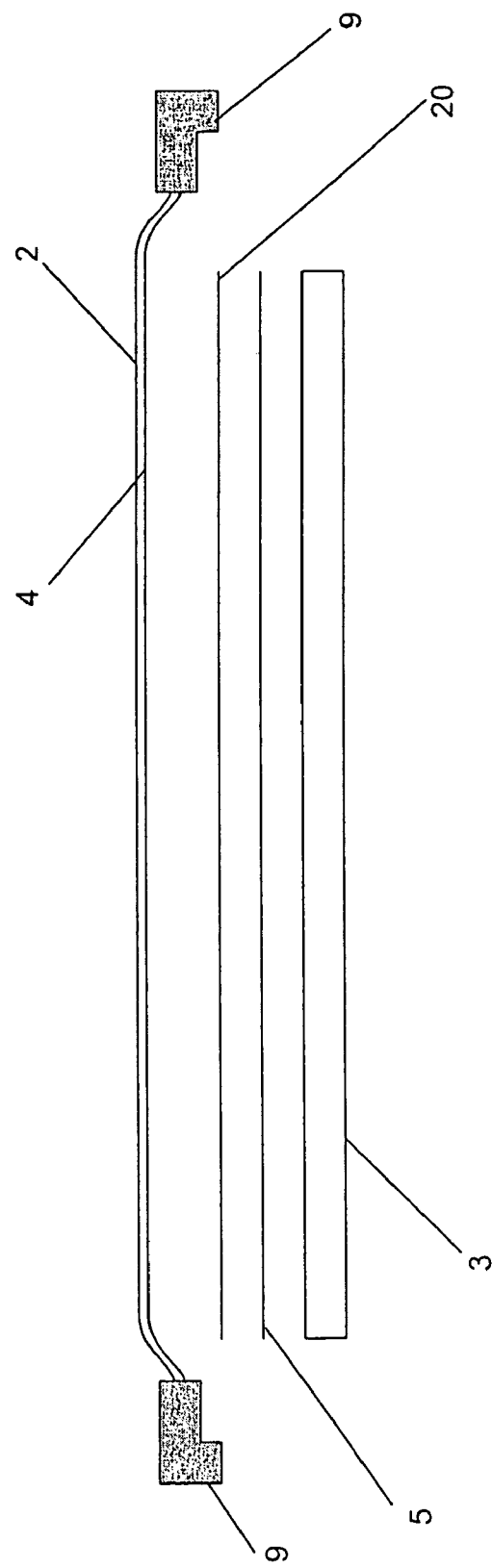
FIG. 2 shows an second embodiment of the sensor capacitive elements of the invention, whereby a double-capacitance is formed.

FIG. 2 shows an alternative embodiment of the sensor capacitive elements of the invention, whereby a double-capacitance is formed. Diaphragm 2 has a conductive surface 4, which forms a capacitance with plate 20, which is comprised of a conductive material. The plate 20 then forms a second capacitance with plate 3, while optional insulation 5 is placed between plate 20 and plate 3. The diaphragm 2 is once again mounted to the housing by a mounting clamp 9. The double capacitance method operates on a similar principle of operation to the embodiment of FIG. 1. However, the circuit connections are somewhat different, as described in further detail below.

Figure 3:
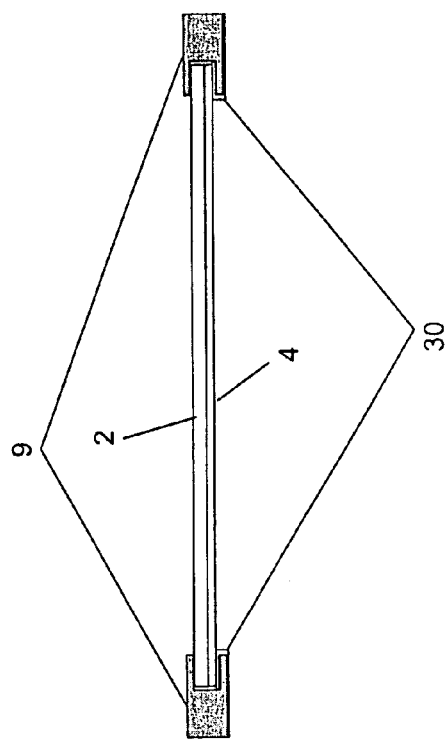
FIG. 3 shows another embodiment of a mounting means for the diaphragm for the capacitive sensor.

FIG. 3 shows an alternative mounting clamp 9 for the diaphragm 2. the mounting clamp 9 is a circular ring shown in cross section. The material from which mounting clamp 9 is made is a sound absorbing substance such as rubber, which prevents vibration from the housing 1 in FIG. 1 from reaching the diaphragm 2 surface. However, the diaphragm has an electrically conductive surface 4 which must be connected to electronic circuitry as indicated in FIG. 1 by connection 11. This connection 11 is achieved, as shown in FIG. 3, by providing a conductive path 30 on the mounting clamp 9. FIG. 3 shows one configuration for achieving acoustic isolation and electrical connection to the conductive surface 4 of the diaphragm 2. If the mounting clamp 9 has a different cross section, or is manufactured from a conductive rubber, the goals of acoustic isolation and electrical connection may still be met.

Figure 4:
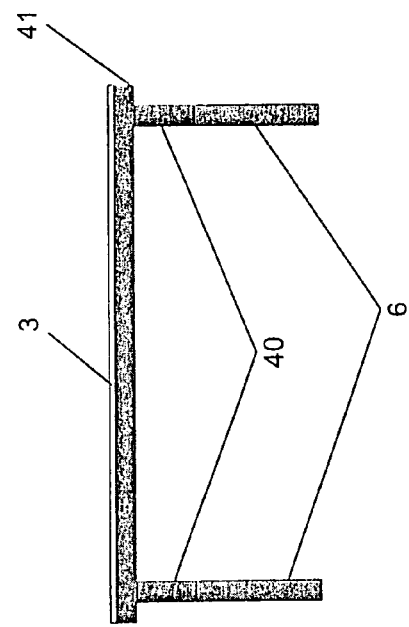
FIG. 4 shows means of ambient sound isolation for the capacitive plate in further detail.
Figure 5:
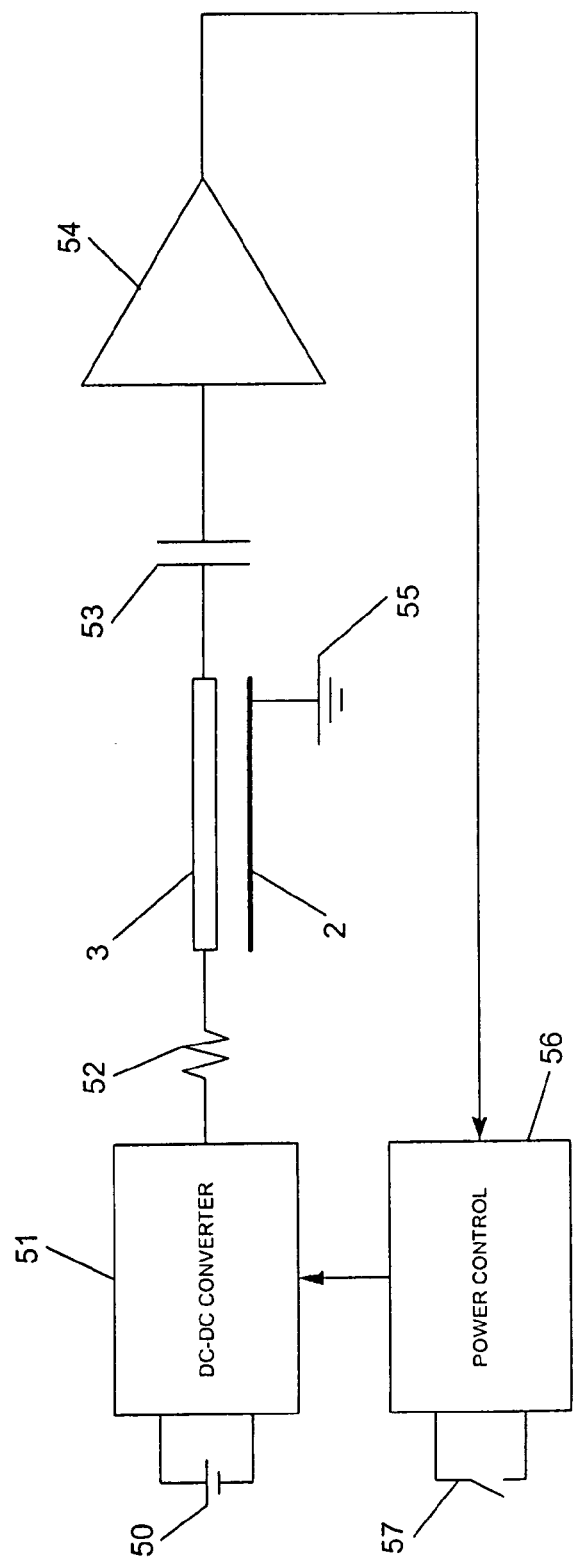
FIG. 5 shows the overall circuit topology of the capacitive sensor when used with a DC-DC charging circuit and associated function.

FIG. 4 shows an important aspect of ambient sound isolation for the plate 3 in more detail. The plate 3 should not vibrate due to housing or external vibrations such as might be produced by ambient noise or handling of the housing 1. The plate 3 must therefore be acoustically isolated from ambient noise sources. This may be achieved by a number of means. A mounting bracket 6 may be constructed with a section 40 which is manufactured from an acoustically absorbent material so that vibrations are attenuated by the section 40. Note that the mounting bracket 6 and the sections 40 are shown as vertical posts. Such mounting may also be achieved by surfaces molded into the housing 1 to support the plate 3, or other means of attachment of the plate 3. The invention simply requires that the plate 3 be acoustically isolated from the housing 1 for optimal performance. FIG. 4 also shows a second alternative to acoustic isolation for the plate 3. The plate 3 may be mounted on an acoustically absorbent material surface 41, such that vibration in the mounting bracket 6 is attenuated by a surface 41. A third method of acoustic isolation is to manufacture the plate 3 from a conductive foam or other electrically conductive, but acoustically absorbent material. The above three methods provide the same function—to acoustically isolate the plate 3. Other methods may be applied to achieve the same goal. An alternative strategy to acoustically isolating plate 3 is to manufacture plate 3 with sufficient mass that acoustic energy does not easily produce vibrations in plate 3. Another alternative methods is to rigidly mount plate 3 to the housing 1, such that the overall plate-housing structure has sufficient mass and rigidity to withstand external acoustic vibration. The method of operation of the preferred embodiment is to develop an electric field in the capacitor formed by the diaphragm 2 and the plate 3 shown in FIG. 1. There are a number of methods for creating this electric field. In a preferred embodiment, a DC source 51, which is a DC-DC boost circuit, is connected to the capacitance via a high-impedance connection 52 as shown in FIG. 5. The DC-DC converter 51 converts low voltage from battery 50 to a high voltage. A voltage of greater than 50V is desired, and significantly higher voltages, on the order of 600V-1000V, are feasible in the device. Larger voltages produce larger gain in the mechanical displacement to electrical signal transfer function. The high voltage passed via resistor 52 to the plate 3 results in the plate 3 being at a high voltage potential relative to the diaphragm 2, which is placed at ground reference potential 55 in a preferred embodiment, since this provides electromagnetic shielding as well as functioning as a capacitive plate. An amplifier 54 is connected to the capacitance sensor via a capacitance 53, which isolates the high DC voltage on the plate 3 from the amplifier, while passing time-varying voltage caused by modulation of the diaphragm-plate distance. The input impedance of the amplifier 54 must be significant in order to allow low frequencies to be passed by the capacitor 53.

Circuit functions for the high voltage implementation of the invention are shown in FIG. 5. The plate 3 is charged by the high potential voltage relative to the diaphragm 2 by DC-DC converter 51. Changes is distance between the diaphragm 2 and plate 3 produce a change in the AC, or time-varying voltage across the capacitor, with high resistance 52 and high input impedance of amplifier 54 preventing the capacitor charge from changing too rapidly. The change in the time-varying voltage across the capacitance is amplified by the amplifier 54, to produce a low-impedance time-varying signal which is a measure of capacitance change, and hence diaphragm motion.

In certain embodiments, the capacitance of the diaphragm-plate capacitor can be extremely low, on the order of 10 pico-Farads. This results in a very small time constant when the capacitance is connected to external circuitry. An important aspect of the high voltage embodiment of the sensor, is the use of very high-impedance DC charging circuitry, and signal amplification circuitry. In a preferred embodiment, this impedance is preferably above 400 Meg Ohms in both the case of the DC charger and the signal amplifier input, although lower impedances are possible. Thus, in FIG. 5, resistance 52 or the source resistance of DC source 51, and the input impedance of amplifier 54, must all be high impedances.

The housing is preferable placed at ground potential, to act as a shield. Shielding requires that the housing 1 be fabricated from an electrically conductive material, or that a conductive surface by applied to the housing 1. The housing 1 and diaphragm 2 therefore form a shielded cavity for the sensor and electronics. It should be noted that either plate 3 or diaphragm 2 may be placed at a high potential, since it is the charge on the capacitance that is of importance, not the polarity. Note that ground 55 is a relative circuit ground connection, not physically connected to earth ground.

Stethoscopes are typically portable instruments, operated on battery power. A further extension of the invention is in the minimization of power consumption. The DC voltage applied across the diaphragm-plate capacitance in the preferred embodiment is generated from a low-voltage source 50 in a typical battery operated device, as shown in FIG. 5. Since the time constant of the capacitive circuit is, by necessity, sufficiently large to allow frequencies below 100 Hz to be sensed, the DC charge on the sensing capacitance remains at an elevated voltage level for some period of time. Therefore, the DC charge circuit 51 may be operated on a pulsed, or intermittent basis, or indeed shut off, once the DC charge is generated on the capacitor plates. This offers substantial power savings over operating the DC charge circuit continuously, providing the preferred embodiment with substantially longer battery life than a continuously operated DC source would provide. The power control circuit 56 is able to control the high voltage level produced by the DC-DC converter 51 for the purposes of low power operation.

Power control function 56 is operated by either a switch means 57, or automatically by sensing the amplifier 54 output signal. Switch means 57 can also take the form of a control signal from a control microprocessor. In the automatic power control mode, the power control function detects whether the diaphragm is in contact with a body by performing signal processing on the amplifier output signal. There are a number of methods for detecting diaphragm-body contact. One method is to detect a heartbeat waveform. A preferred method is to sense low frequency signal energy in the amplifier output, since this is typically absent when the diaphragm is not in contact with a body.

Since the output signal amplitude from the amplifier 54 is dependent on the DC voltage, the power control function 56 may also be employed to monitor amplifier output and act as an automatic or manual gain control for the sensor, adjusting DC voltage to control amplifier signal output amplitude. This provides the advantage of preserving battery power, as well as providing consistent signal levels. Further, while gain control may be provided at later stages of amplification, there is an advantage to adjusting front end signal level to avoid clipping and to maximize signal-to-noise ratio of the overall amplification process.

Automatic gain control is also optionally implemented in amplifier 54. This is especially important as a means of preventing excessively loud signals from being generated. Amplifier 54 thus optionally includes an automatic muting or attenuation means which is triggered by significant signal levels. These transients typically occur when the diaphragm makes or breaks contact with a body, or when the diaphragm is moved across a body.

Figure 6:
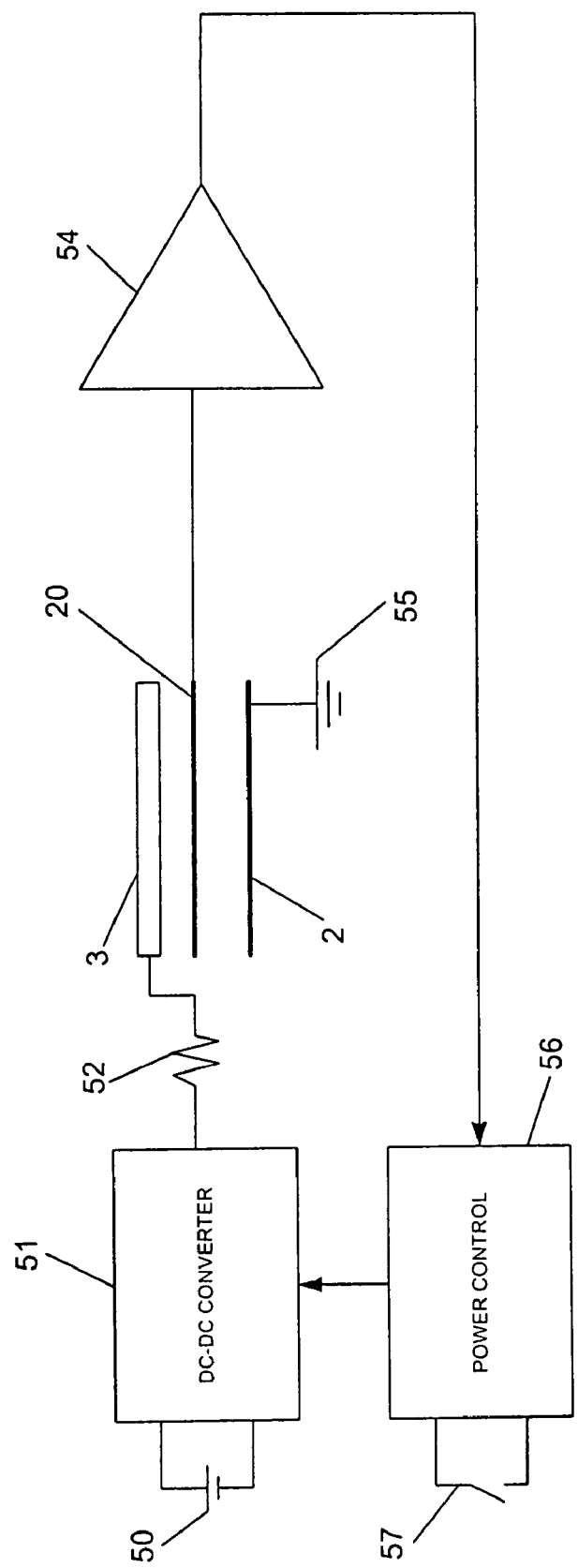
FIG. 6 shows a triple plate capacitance form of the sensor.

An alternative method of creating a capacitive sensor is shown in FIG. 2, with electrical connections shown in FIG. 6. In this implementation, sensor plate 20 is connected to the amplifier input, while plate 3 is at a high voltage as before, and diaphragm 2 is at ground reference potential 55 as before. Circuit operation is as described previously. However, the capacitance formed by plate 20 and the diaphragm 2 serves the dual purpose of sensing and isolating the high DC voltage on plate 3 from reaching the amplifier. It is also possible to exchange plate 20 and plate 3 in FIGS. 2 and 6 to construct a capacitive sensor, and such a structure is electrically equivalent to the circuit shown in FIG. 5.

Figure 8:
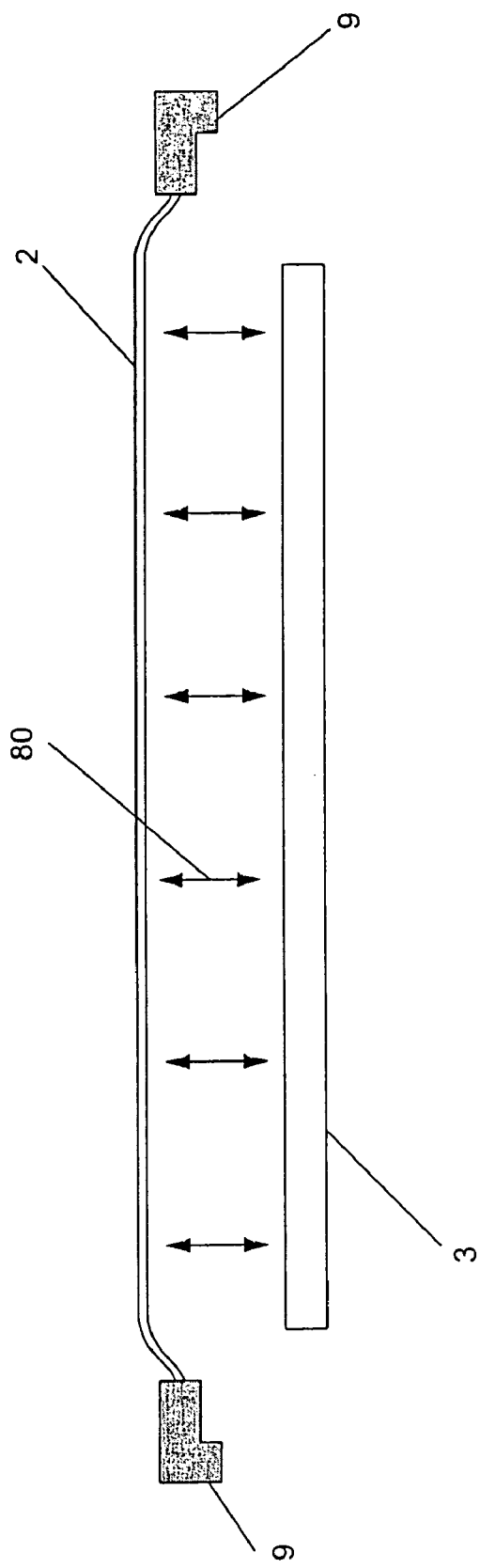
FIG. 8 shows the capacitive sensor wherein the diaphragm, plate, or both are permanently charged such that an electric field exists between the plates obviating the need for a capacitive charging circuit.

An alternative method of establishing a voltage across the diaphragm 2 and plate 3 is shown in FIG. 8 whereby diaphragm 2, plate 3 or both are fabricated with an electret or permanently charged material that maintains a permanent surface charge on one or both elements, setting up an electric field 80 with no external DC drive circuitry. This has the significant advantage that no DC-DC converter is now required, and the time-varying voltage across the diaphragm-plate capacitance may be amplified directly. This method is commonly used in small low cost electret condenser microphones. However, the present invention is unique in that one of the capacitive plates forms a stethoscope diaphragm, allowing physical contact with the body from which sound is to be detected. The manufacture of an electret implementation may be achieved by adhering an electret material to the inside of the diaphragm. Alternatively or additionally, plate 3 may be constructed with an electret surface, or an electret material may be adhered to plate 3. The salient issue is that an electric field must exist between the diaphragm 2 and plate 3, and the invention includes any means by which such a field may be created, either actively using a DC power source, or by using materials which set up a permanent electric field between diaphragm 2 and plate 3. In a semiconductor embodiment, the electret material can be deposited as part of a semiconductor fabrication process. Referring to FIG. 1, it is also potentially advantageous to place a dielectric insulator 5 between diaphragm and plate, even in the electret embodiment shown in FIG. 8. It is also of value in the electret embodiment to facilitate diaphragm motion in excess of 0.1 mm due to static pressure against the body, and also to utilize the change in static capacitance to control or modulate gain and frequency response of the electret transducer. This is not typical of electret microphones in which motion is limited to a few microns, and the capacitive spacing is limited to tens of microns, the intent being that static displacement be limited or tightly controlled. Such diaphragm stiffness would reduce diaphragm sensitivity to acoustic energy. Since a stethoscope diaphragm is typically 25 mm or greater in diameter, significant stiffness would be required to limit diaphragm motion to less than 0.1 mm or greater as defined in this invention. The electret embodiment of this invention is thus unique in that a large diaphragm 2 of at least 25 mm, but potentially as small as 15 mm diameter is spaced from the fixed plate 3 by at least 0.1 mm spacing and the diaphragm 2 is sufficiently flexible to undergo displacements approaching 0.1 mm under pressure from the body during use. It is also unique to exploit such displacement to control gain and bandwidth of the transducer, under influence from a user exerting pressure to control such parameters.

Figure 7:
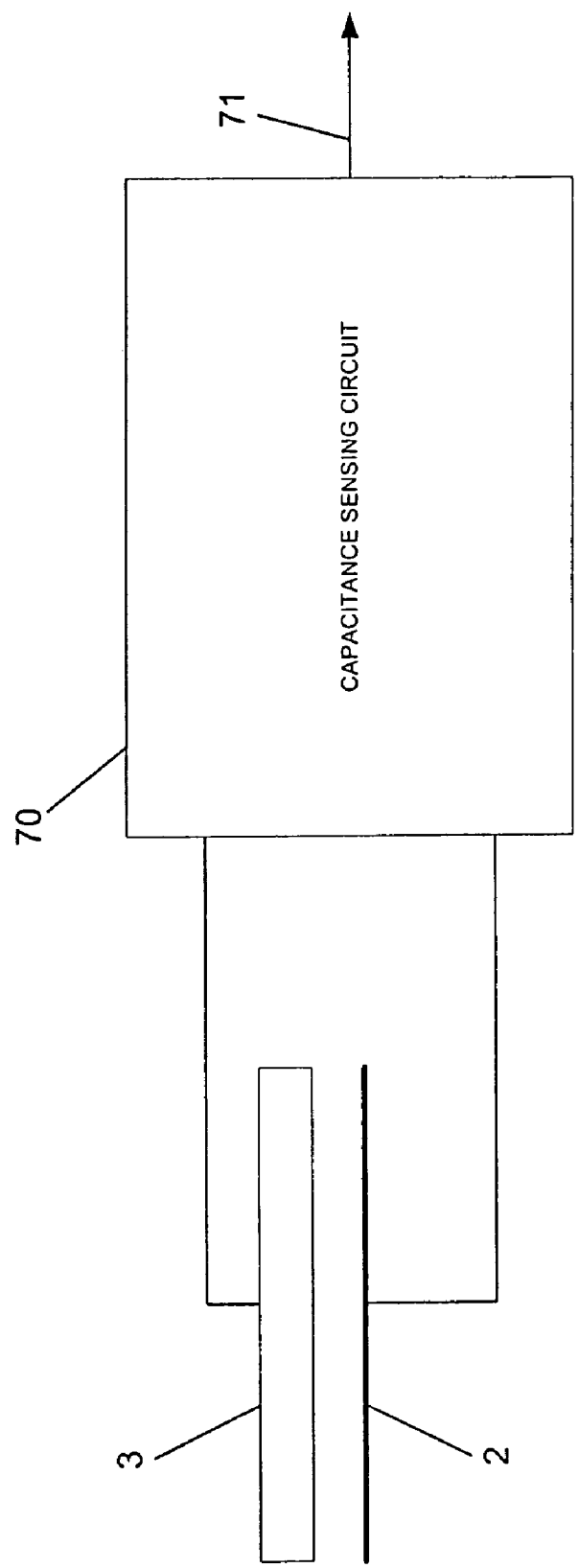
FIG. 7 shows the sensor used in a generalized capacitive sensing circuit.

An alternative method of sensing capacitive change in the sensor is shown in FIG. 7. The plate 3 and diaphragm 2 conductive surfaces are connected to a capacitance sensing circuit 70. The output 71 is an electrical signal, or digital message which transmits the capacitance measurement as a function of time. There are a number of methods of sensing capacitance change due to diaphragm displacement. A few examples are:

a. Connecting the diaphragm-plate capacitance to an oscillator, and converting frequency variation due to capacitance change into a voltage representative of diaphragm motion.

b. Connecting the capacitance to a resonant circuit and measuring changes in resonant characteristics with changes in capacitance.

c. Connecting the capacitance to a charging circuit, whereby the charging and/or discharging time of the circuit are converted to a voltage measurement representative of capacitance change.

d. Connecting the capacitor to a digital measurement and conversion means, whereby capacitance change results in changes in pulse width or digital values.

e. Connecting the capacitance as a timing element in an analog-to-digital converter circuit whereby digital codes are a function of the capacitance.

All of these methods are based on the fundamental aspect of the invention whereby a capacitance is formed by the diaphragm in conjunction with another element, providing a direct transducer means from diaphragm motion to capacitance change, to electrical measurement. In essence, the above methods use the capacitance as an element in a circuit whose time constant affects electrical waveforms.

The above methods are particularly suited to a semiconductor implementation of the capacitive sensor, since these electronic functions can be implemented very effectively on a semiconductor integrated circuit. Therefore, this invention covers capacitive sensors for body sound detection in which the diaphragm makes direct contact with the body, and the capacitive sensor and associated conversion electronics are combined onto a semiconductor substrate to form an integrated sensor and circuit system.

Figure 9:
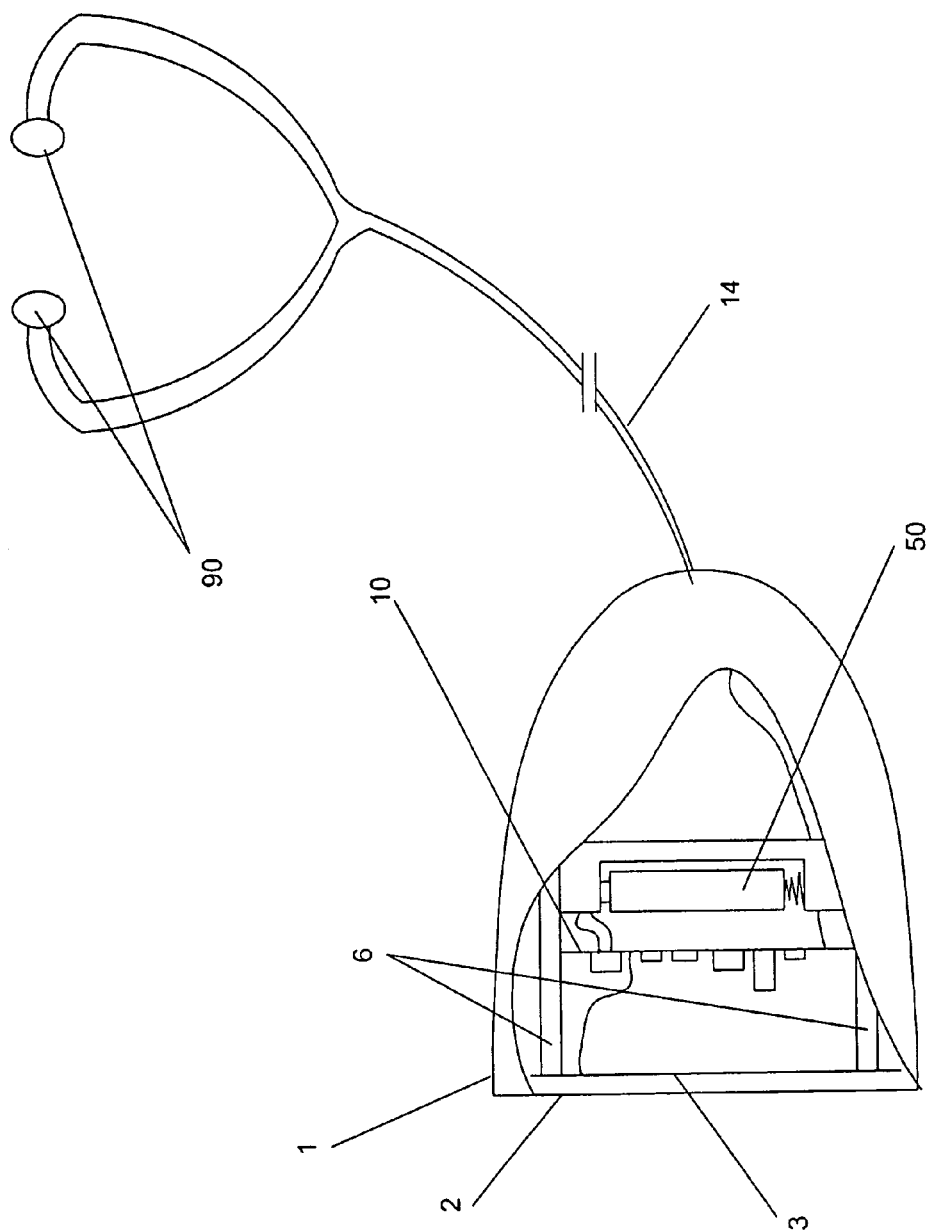
FIG. 9 shows in schematic form and not to scale a stethoscope including the capacitive sensor of the invention.
Figure 10:
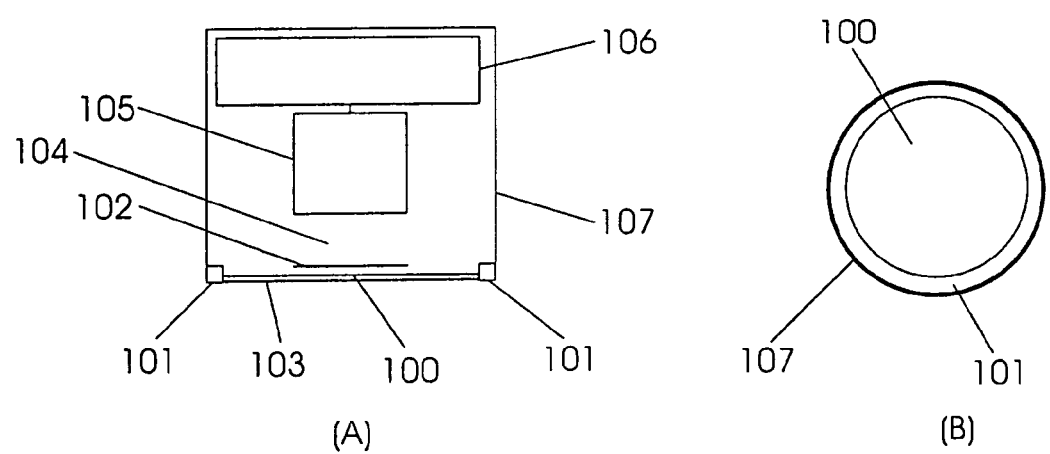
FIG. 10 shows a magnetic sensor embodiment wherein a magnetic material is adhered to or an integral part of a diaphragm.

FIG. 9 shows in schematic form only a stethoscope with the sensor or transducer of the invention. The sensor is much the same as that illustrated in FIG. 1, with the sensor elements shown enlarged in a cutaway view. The housing 1 (shown enlarged and not to scale compared to the remainder of the stethoscope, and partially cut away) houses the elements of the sensor and associated components. The diaphragm 2 is mounted such that it can easily be placed in proximity to a body for sensing sounds. A plate 3 is mounted via a mounting bracket 6 placed behind the diaphragm 2, and parallel to it. Electronic circuit 10 is placed within the housing 1, and powered by a power source 50. An electrical connection 14 transmits audio signals to audio output transducers 90. Further details of the sensor are shown in FIG. 1 and other drawings, and may not be visible in the embodiment as illustrated in FIG. 9.

Note that FIG. 9 illustrates just one embodiment of the invention as used in a stethoscope. Various methods of housing the sensor, placing electronic circuitry within the same or different housing, partitioning electronic circuit functions within the same or different housing, and communicating the signals to the audio transducer are possible without deviating from the fundamental structures and methods disclosed herein. FIG. 9 also shows only a capacitive sensor embodiment of the invention. This invention covers capacitive, magnetic and optical transducer means housed in a stethoscope and figures depicting such transducer embodiments would illustrate the same overall stethoscope structure as that shown in FIG. 9 for the capacitive sensor embodiment.

Stethoscope diaphragms are subject to long term wear and breakage. In a mechanical stethoscope, replacement of the diaphragm is a simple process. In the case of a capacitive diaphragm as described in this invention, it is potentially beneficial to encapsulate the diaphragm 2 and plate 3 in FIG. 1, along with some electronic circuitry 10, in a sealed container that can be easily removed from the main body of the stethoscope. This allows the diaphragm and associated components to be replaced simply, while maintaining a sealed environment for high voltage, fluid, or other elements of the capacitive sensor which exist behind the diaphragm, and which are best kept sealed from atmospheric contaminants, or should not be touched by users. Similarly, the structures shown in FIGS. 10, 11, 12, 13, 14 and 16 for magnetic and optical embodiments can be housed in separable housings that can be attached or detached from a stethoscope or other instrument. The invention thus allows for such elements of the invention to be housed in such a sealed housing, for convenient replacement or repair.

The sensor, enclosed in housing 1 or housing 107 can be used as a peripheral audio sensing device, which can be connected to an external audio recording, transmission or amplifying and reproduction means. Alternatively, housing 1 or housing 107 is physically attached to a stethoscope, and forms part of the overall stethoscope housing.

While the preferred capacitive embodiment is in the form of a capacitive sensor with a moving diaphragm and fixed plate, it is feasible to form a capacitor with both electrodes being flexible. Such a design includes a diaphragm capacitance formed by two flexible surfaces separated by a dielectric that allows modulation of the distance between the two electrodes due to motion of the two-plate diaphragm. The invention is thus intended to cover any method that comprises a diaphragm acting as part of a capacitive sensor.

FIGS. 10, 11, 12 and 13 show magnetic transducer embodiments of the invention. While the capacitive transducer invention discloses a diaphragm that modulates an electric field, the magnetic diaphragm modulates a magnetic field, operating as follows.

Referring to FIG. 10(A), diaphragm 100 comprises a substrate, and a magnetic material 102, such as a ferro-electric layer. This magnetic material 102 is shown schematically as separate from the diaphragm substrate, however it is to be considered mechanically attached to the diaphragm. A magnetic sensing element 105 such as a Hall element sensor or sensing coil is placed behind the diaphragm, and spaced from it via space 104 which is at least 0.1 mm from any diaphragm elements, the spacing being sufficient to ensure a spacing always exists even during normal use when the diaphragm is placed against the body. The magnetic sensing element 105 detects changes in diaphragm displacement by converting magnetic field changes in spacing 104 to electrical signal changes. The electronic circuit 106 is connected to the magnetic sensing element 105, to convert the raw electrical sense signal to a signal-conditioned output. The magnetic sensing elements, and optionally the electronics, are placed within housing 107 to provide magnetic and electric shielding against external interference. The diaphragm optionally includes magnetic shielding 103.

Referring to FIG. 10(B), diaphragm 100 is mounted within housing 107 via a circumferential mounting means 101 which allows freedom of movement for the center of the diaphragm. Since spacing 104 in FIG. 10(A) allows for unimpeded motion of the center of diaphragm 100, the diaphragm 100 is able to move in the same way as that of an acoustic stethoscope, thereby maintaining acoustic characteristics of an acoustic stethoscope diaphragm. Diaphragm 100 is mounted so that it can directly contact the body for body sound sensing. Diaphragm 100 directly influences the magnetic field in space 104 since the magnetic material 102 is integral to, or mounted onto, diaphragm 100.

The displacement of diaphragm 100 comprises a static displacement and a dynamic displacement. The static displacement affects the gain and frequency characteristics of the signal output by electronic circuit 106, providing the user with control over signal characteristics through application of variable pressure on the diaphragm.

Figure 11:
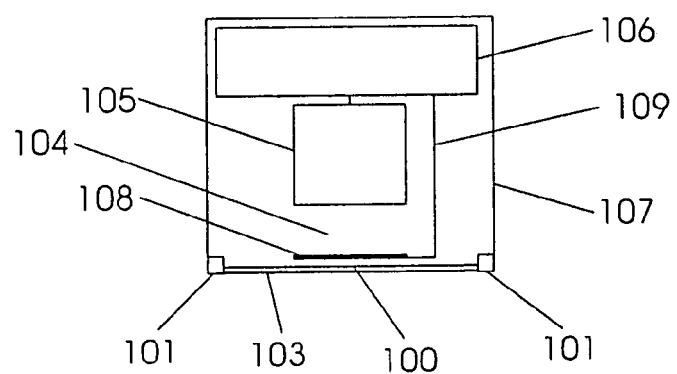
FIG. 11 shows a magnetic sensor embodiment wherein the diaphragm has a coil or printed circuit coil as part of the diaphragm and magnetic assembly.

An alternative to the magnetic embodiment is shown in FIG. 11, and comprises a diaphragm 100 with an electrically-conductive material 108 adhered to or deposited onto diaphragm 100. The conductive material is connected via connection 109 to an electrical circuit 106 such that a magnetic field is produced behind the diaphragm in spacing 104, and changes in magnetic field due to diaphragm motion can be converted to electrical signals by circuit 106. The conductive material 108 in this case might be a conductor which acts like a coil, such conductive pattern being printed, etched or adhered onto the diaphragm. A unique aspect of this magnetic embodiment is that the diaphragm 100 is free to move mechanically due to spacing 104 and mounting means as shown in FIG. 10(B), and the transducing means does not impede diaphragm motion. Further, the mechanical housing 107 allows for the diaphragm to contact the body directly for sensing body sounds, without any intervening air layer between the diaphragm 100 and vibrating surface of the body. Magnetic shielding 103 is optionally included on the diaphragm, so that magnetic fields inside the sensor housing 107 are shielded from interference from external magnetic or electric fields. Such shielding 103 includes materials such as mu-metals, or electrically conductive materials.

The embodiment shown in FIG. 11 can operate in one of two ways. In the first case, discussed above, the conductor 108 creates a magnetic field that is sensed by sensor 105. In the second case, the conductor 108 senses the changes, and element 105 creates the magnetic field rather than sensing it. In either case, a magnetic field exists in spacing 104, and the elements 105 and 108 act in concert to set up the field and sense changes in it due to diaphragm motion.

Figure 12:
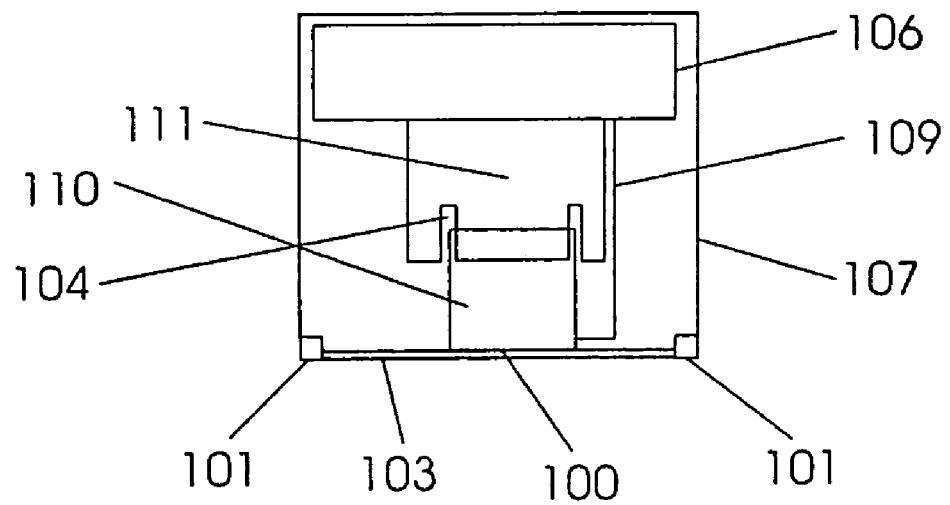
FIG. 12 shows a magnetic sensor embodiment wherein a coil is mounted normal to the diaphragm and a permanent magnet is placed behind the diaphragm to form a dynamic microphone structure.

FIG. 12 shows another magnetic embodiment, in which a coil 110 is mounted normal to the rear side of diaphragm 100. A permanent magnet 111 is mounted such that the magnetic field in coil 110 changes when diaphragm 100 moves due to vibration. Coil 110 is connected via connection 109 to an electronic circuit 106 which produces an electrical signal based on magnetic field changes due to motion of diaphragm 100. Diaphragm 100 is mounted as described above, to provide contact with the body and unimpeded motion, since spacing 104 is greater than 0.1 mm and provides sufficient spacing to ensure that some spacing exists during use.

Figure 13:
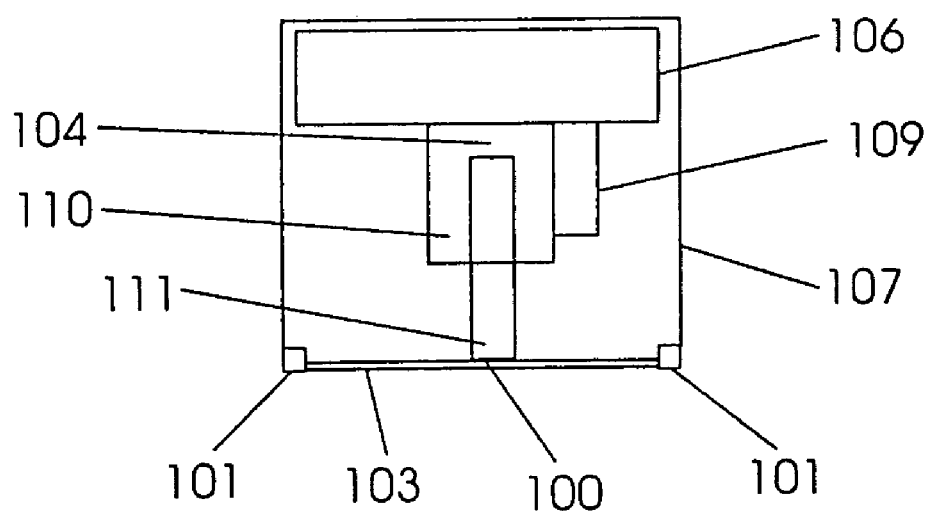
FIG. 13 shows a magnetic sensor embodiment wherein a magnet is mounted normal to the diaphragm with a stationary coil used to sense diaphragm motion.

FIG. 13 shows an embodiment which is functionally analogous to that shown in FIG. 12, except that structurally the coil and magnet are reversed such that coil 110 is fixed, and magnet 111 is mounted to diaphragm 100 and moves with the diaphragm. In other respects, the embodiment in FIG. 13 is as described above for FIG. 12.

In FIGS. 12 and 13, the mounting of the coil or magnet normal to the diaphragm might optionally require a stabilizing member attached to the housing or other mechanical element to hold the normal magnet or coil in place. This invention covers such modifications, since the fundamental magnetic field modulation method is still applicable to such embodiments.

Figure 14:
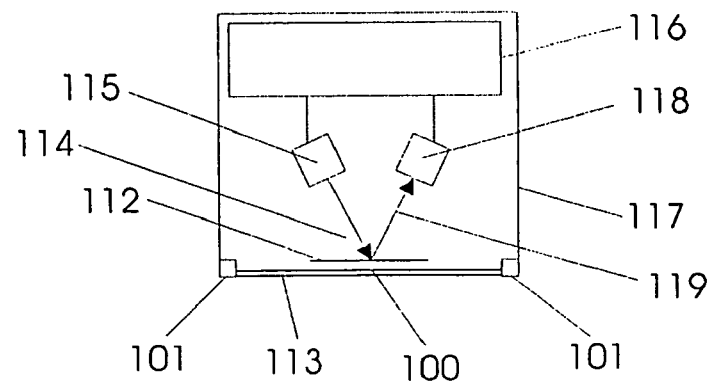
FIG. 14 shows an optical sensor embodiment wherein a light beam is reflected from the back of the diaphragm, and changes reflected light are converted to an electrical signal.

An embodiment which uses optical diaphragm motion detection is shown in FIG. 14. In this embodiment, the diaphragm 100 includes a reflective means 112, such as a layer of optically-reflective material with a pattern which affects reflectance. The reflectance means 112 might be adhered to the diaphragm substrate or printed or etched onto the substrate. In this embodiment, light source 115 emits a visible or infrared or laser light beam 119 which strikes reflectance means 112 and is reflected to light sensor 118, the beam 119 being modified due to motion of diaphragm 100. These optical elements are located within housing 117. Electronic circuit 116 provides drive and sensing signals for emitter 115 and detector 118. The diaphragm 100 is mounted in housing 117 by circumferential mounting means 101. Spacing 114 provides the light path, and ensures that diaphragm 100 has sufficient spacing for static and dynamic displacement as discussed previously in the case of the capacitive embodiment. The optical elements are housed in housing 117 and diaphragm 100 optionally includes a light and/or electromagnetic shield or protect optical and electrical elements from external interference.

The change in light signal 119 in one embodiment shown in FIG. 14 is an angular or intensity change, and is in proportion to the diaphragm displacement. Angular change in reflection is produced by changes in the point at which reflection occurs due to the change in geometry of the light path 119 caused by diaphragm motion. Detector 118 is thus sensitive to positional or angular changes in reflection. The reflective element 112 could also comprise a reflective mirror or lens structure whereby the light hits the structure, and is refracted or reflected by a mirror or lens which modifies the light path or intensity that is reflected to the detector 118.

Figure 15:
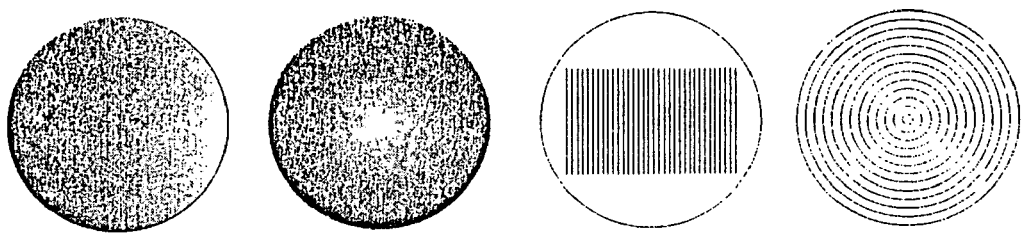
FIG. 15 shows various diaphragm optical reflection patterns that produce changes in the reflected light signal as the diaphragm position changes, and the point of reflection changes.

Intensity change is produced the embodiment in FIG. 14 if diaphragm 100 has a reflective layer 112 that has a variable reflective characteristic that is a spatial function such as those shown in FIG. 15. In this case, as the diaphragm 100 vibrates, the reflection signal 119 changes intensity by being reflected off a location in the pattern that changes with diaphragm displacement.

In FIG. 15(A), the pattern is linear and constantly variable in an analog (continuous) manner, producing an analog signal variation in light signal 119. In FIG. 15(B), this same concept applies, except that the reflectance is a function of diaphragm radius, and the pattern is radial as shown in FIG. 15(B). This has the advantage that the diaphragm can be mounted at any rotational angle in housing 117.

The pattern shown in FIG. 15(C) produces a pulsating variation in light signal 119, as the light beam reflects alternately off a light or dark line. These pulses are then converted to an electrical signal that is a function of diaphragm displacement. FIG. 15(D) operates on the same principle except that the alternating pattern is radial, allowing for diaphragm mounting at any rotational angle in housing 117. The patterns shown are schematic representations, and do not show the resolution that is required to produce high signal-to-noise ratio audio signals that accurately measure diaphragm displacement. The line spacing for the digital modulation schemes shown in FIGS. 15(C) and 15(D) is on the order of more than 10 lines per millimeter, and preferably greater than 50 lines per millimeter.

While some diaphragm spatial reflectance functions are shown in FIG. 15, this invention covers any embodiment in which a diaphragm is placed against the body, and the rear surface of the diaphragm has optical characteristics that allow for a reflected light signal to be modulated by diaphragm motion.

This optical detector embodiment of FIG. 14 is unique in that a diaphragm 100 can contact the body directly due to mounting 101 and housing 107, and the same diaphragm produces changes in the optical signal 119 reflected from the diaphragm and converted to a signal representative of diaphragm motion.

Figure 16:
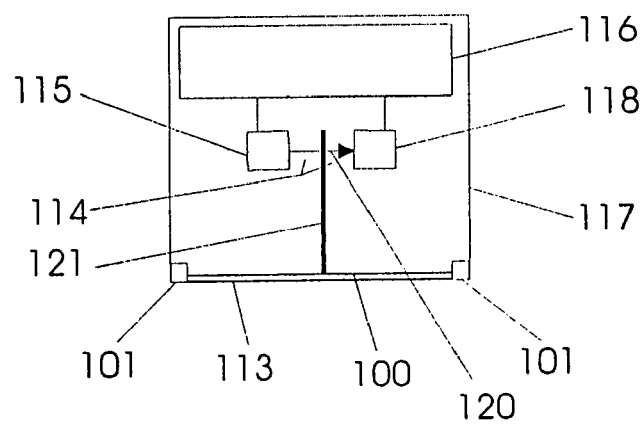
FIG. 16 shows a optical sensor embodiment wherein an optical film or other structure is mounted normal to the diaphragm, such that the structure interferes with a transmitted light source in order to produce an electrical signal that measures diaphragm motion.

In a second optical detection embodiment, shown in FIG. 16, a transmissive method is disclosed, in which the light signal 120 is transmitted from light emitter 115 through a transmissive optical element 121. Spacings 114 in all directions around element 121 ensure that diaphragm motion is unimpeded during use allowing for both static and dynamic displacement of diaphragm 100. Light signal 120 can be visible, infrared and can be a laser light signal. The optical elements are housed in housing 117 and diaphragm 100 optionally includes a light and/or electromagnetic shield or protect optical and electrical elements from external interference.

In FIG. 16, the optical element 121 is mounted to be moved directly by diaphragm 100 motion, and diaphragm 100 can be placed against the body during use, the structure thereby providing very direct signal conversion.

Figure 17:
FIG. 17 shows the transmissive light patterns that are applicable to the transmissive reflector shown in FIG. 16.
Figure 17:
Figure 17:

FIG. 17 shows some embodiments of the transmissive element 121. In FIG. 17(A) a transmission medium is shown that is a linear function of displacement. FIG. 17(B) shows a circular function, and FIG. 17(C) shows a digital pattern which is interrupted by diaphragm motion to produce a pulsating output signal. Transmissive medium 121 can, in one embodiment, be attached to the housing 117 or other element, in order to ensure that the optical element 121 is mechanically stable. However this attachment does not unduly modify the dynamics of diaphragm 100. This invention covers all transmissive patterns that would result in modulation of light signal 120, not only those shown in FIG. 17. Another transmissive element is a lens structure that modifies the light signal 120 by means of refraction, and this invention includes such methods.

In the case of an optical embodiment, the spacing between any diaphragm elements and other elements can be as low as 0.1 mm but can be of the order of a few millimeters as well. The primary criterion is that the motion of the diaphragm 100 produce sufficient optical beam modulation such that electronic circuit 116 can produce an audio signal that provides a signal-to-noise ratio in excess of 35 db in the audio signal, or produces a signal that can further be processed to produce an audio signal with signal-to-noise ratio in excess of 35 db. This requirement establishes requirements on the resolution of optical elements. Thus the beam width of signal 119 in FIG. 14 or beam 120 in FIG. 16 must be sufficiently narrow to facilitate sufficient signal resolution. The reflectance patterns must also be of sufficient resolution to provide adequate beam modulation. The detection capability is thus a function of beam width, detector sensitivity and noise, reflectance pattern, and beam geometry. It is the final signal integrity that controls these parameters, and hence the requirement must be placed on signal-to-noise ratio, rather than the elements specified separately.

The optical embodiments also have the inherent capability to use static and dynamic displacement to provide gain and frequency control. Since the optical signal can determine actual position or actual displacement from the unpressured null position, circuit 116 can modify gain, frequency response or other signal parameter as a function of steady state or static diaphragm position. Thus the user can, as in the case of capacitive or magnetic embodiments, control signal parameters through static pressure on the diaphragm.

Referring to FIG. 4, which shows the capacitive embodiment of the invention and specifically the mounting of stationary internal elements, wherein the stationary structure is the capacitive plate 3, the magnetic embodiment and optical embodiment have an analogous requirement for their static elements to be resistant to vibration. Thus in FIGS. 10 and 11, magnetic element 105 must be held stable, in FIG. 12 magnet 111 must be held stable, in FIG. 13 coil 110 must be held stable, in FIGS. 14 and 16, light emitter 115 and light detector 118 must be held in an immobile stabilized position so that acoustic energy does not produce undesirable motion. In all of these embodiments, the methods shown in FIG. 4, and discussed above apply. Thus a mounting means which either decouples the static elements listed from other vibrating elements such as the housing are required, or the static elements listed must be held in a stable position by mounting on a mass that is resistant to vibration, or mounted rigidly to the housing so that resistance to vibration is achieved.

In all of the above embodiments, the diaphragm is in contact with the body for vibration detection due to housing construction which allows for such contact, the diaphragm is unimpeded by mechanical to electrical coupling mechanisms in contact with the diaphragm, and the diaphragm motion directly controls an electrical or optical signal. Such direct coupling between acoustic and electrical signaling, while maintaining the mechanical and acoustic characteristics of an acoustic stethoscope diaphragm, are unique aspects of this invention, allowing acoustic stethoscope sound characteristics to be transduced to the electrical domain for further electronic signal processing. A unique aspect of the present invention is that diaphragm movement is directly transduced to an electrical signal, such diaphragm being in direct contact with the body. Thus there is no air gap between the element that senses body sounds and the vibrating body itself. This offers a number of novel means for reducing ambient noise pickup by the transducer.

In typical electronic stethoscopes, there is an air cavity between a non-electronic diaphragm and the electronic transducer, or in the absence of a diaphragm an air cavity between the body and the transducer. In mechanical or acoustic stethoscopes, the transducer, as it were, is the listener's eardrums and the entire chestpiece and tubing system forms a closed cavity. In order to efficiently transmit body sounds to the transducer, this body-transducer cavity must be closed to ambient sound and the atmosphere external to the stethoscope. If the cavity is not sealed but leaks in some way, acoustic energy essentially cannot pass from the body or body-contact diaphragm to the transducer. One problem with this prior art is that the closed cavity forms an acoustically resonant space as is well described in texts on cavities, pipes and acoustic waveguides. In this closed cavity, standing waves build up and ambient noise which enters the space echoes and reverberates, and is transduced along with body sounds. Sometimes a pressure equalization opening is provided in the otherwise sealed cavity, however such an opening is designed and sized to essentially prevent sound transmission and only for pressure equalization.

In the present invention, since the diaphragm detects body sound directly, the air pressure in the space behind the diaphragm is not essential to the process of detection of body sounds. This offers the unique possibility to open the transducer housing behind the diaphragm to the ambient atmosphere so that standing waves and resonance are reduced or eliminated. This produces a counterintuitive result wherein an aperture in the transducer or stethoscope housing sufficiently large to allow ambient sound to enter the actually reduces the effects of ambient sound by preventing the sound from building up inside any housing cavity or cavities. While ambient noise still reaches the diaphragm, it has a more natural quality that is less annoying than a resonant reverberant version of the ambient noise. This is a very surprising result, that opening the transducer reduces the annoying aspects of ambient noise.

Figure 18:
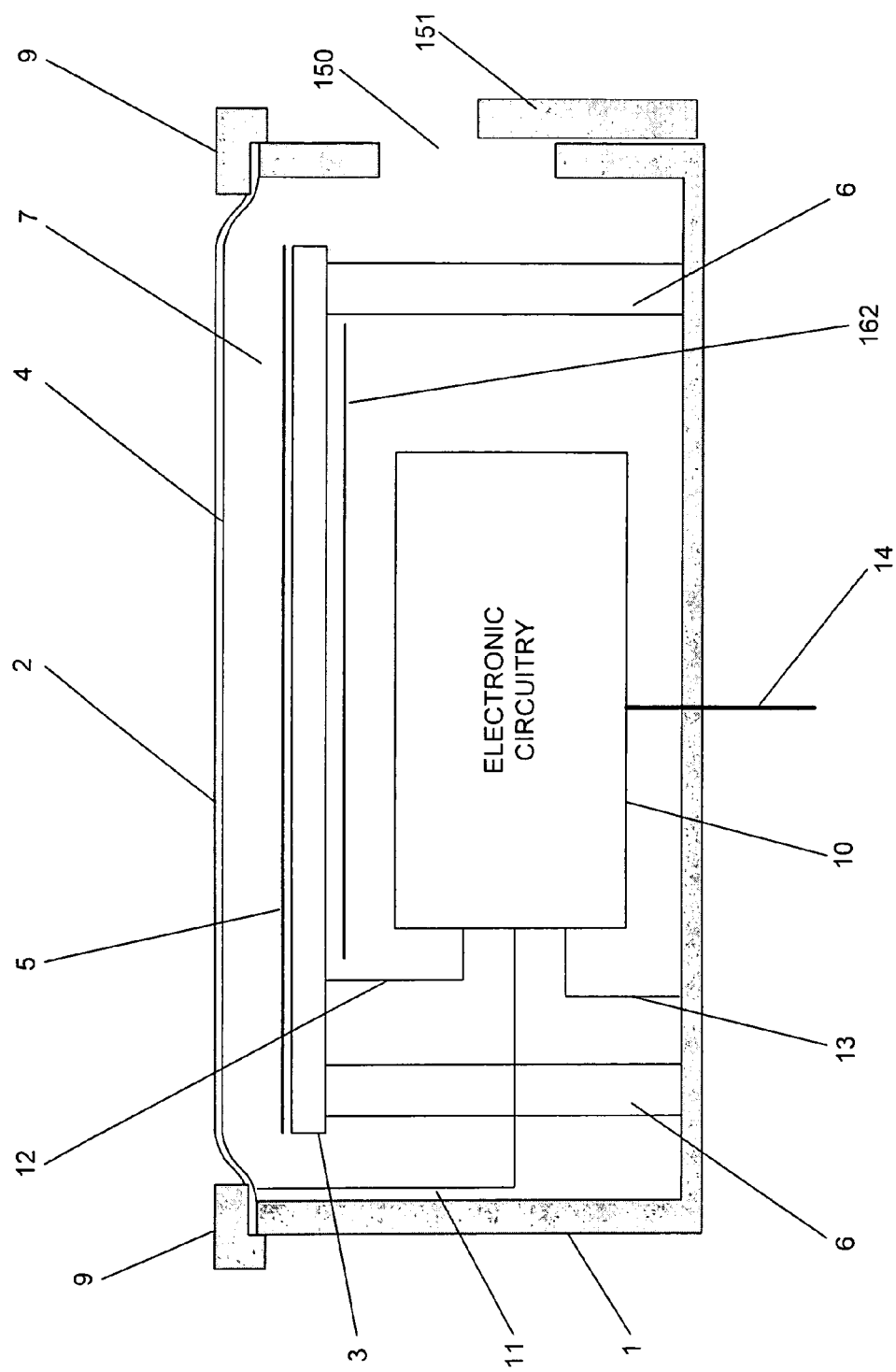
FIG. 18 shows a capacitive transducer housing modified to provide air and sound transmission into the transducer housing inner cavity and specifically to the space behind the diaphragm.

This open housing is shown diagrammatically in FIG. 18 for the capacitive transducer embodiment. Aperture 150 provides an opening between the inner cavity of housing 201 to the outside atmosphere. Sound entering the housing can impinge on the rear surface of diaphragm 202. The aperture 150 comprises one or more openings in housing 201. Aperture 150 is sufficiently large to allow essentially unimpeded acoustic transmission from outside the housing 1 to inside the housing cavity. This is distinct from openings that allow only pressure equalization, or are placed in a housing for the purposes of display or control openings, but are otherwise designed to block sound transmission. Aperture closing element 151 provides the facility to close the aperture(s) 150 allowing the user to control the degree to which aperture 150 is open or completely closed. This is convenient for situations where the user might wish to maintain a closed housing against moisture, humidity or other substance entering housing 201. While FIG. 18 is a schematic representation of a housing that allows atmospheric air and sound into the cavity of housing 201, this invention covers any method by which this open-close function is implemented. This includes, but is not limited to, rotating rings with openings that align with or block the apertures depending on position, or a multi-element housing structure wherein one part of the housing moves with respect to other parts of the housing to block or open the aperture(s).

Figure 19:
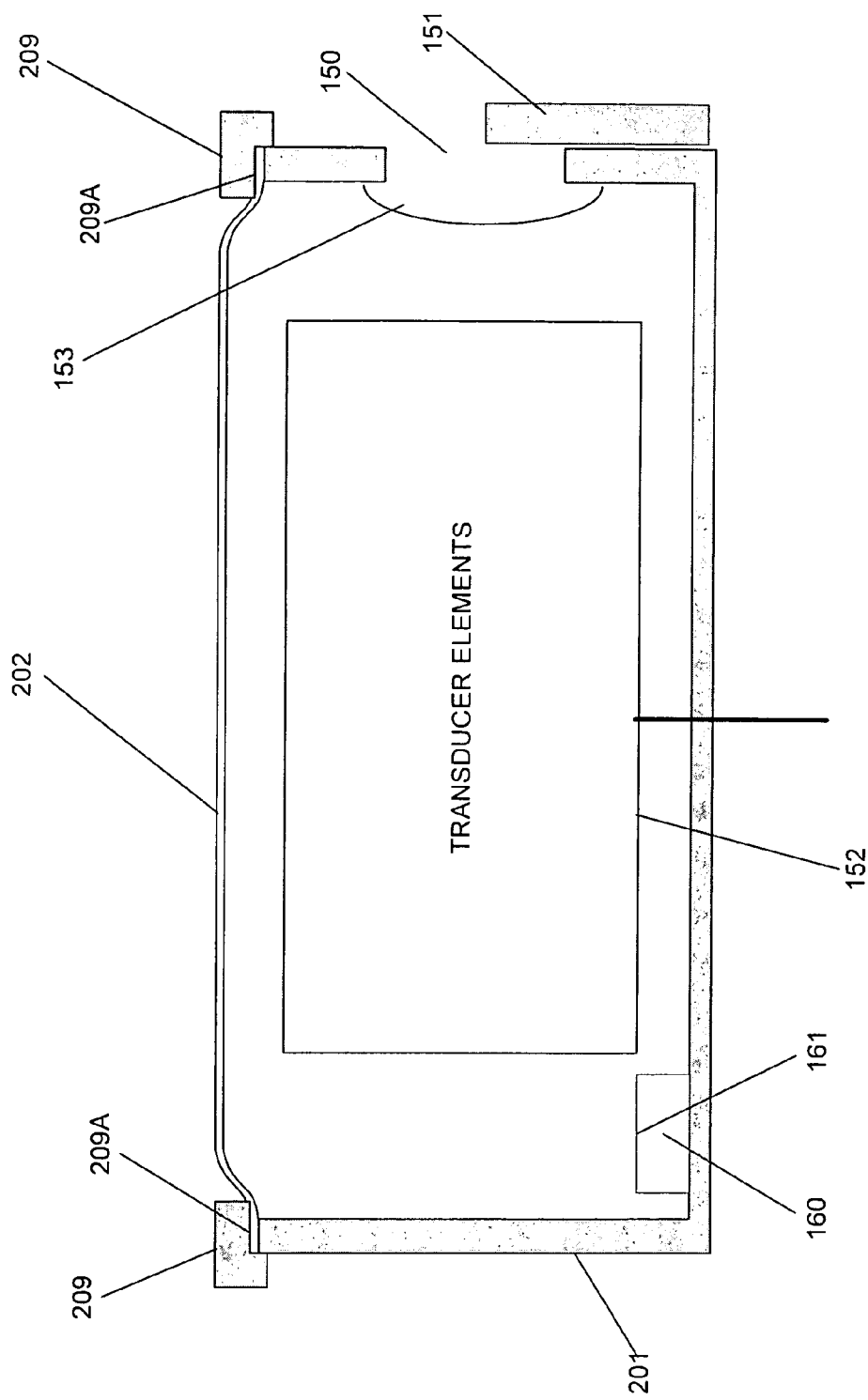
FIG. 19 shows a general transducer housing modified to provide air and sound transmission into the transducer housing cavity, as well as means to close the cavity to moisture while maintaining transmission of sound into the cavity.

FIG. 19 shows the open housing 201 with aperture 150 and closing mechanism 151 shown schematically for the capacitive, magnetic or optical transducers 152 in the present invention. The open housing is thus applicable to all transducers in the present invention. Further, since stethoscope chestpieces in the prior art rely on closed transducer housings as a fundamental requirement of their operation, the open housing or chestpiece is a unique modification for any stethoscope, regardless of transducer mechanism. All such open housing embodiments are unique in that they are structured with one or more apertures or openings to allow external sound to enter into the housing which contains the body sound transducer, with the intent of reducing or eliminating standing waves or resonances in cavities within the body sound transducer housing.

FIG. 19 shows an optional moisture barrier 153 which can be place in housing 201 to prevent moisture and humidity from entering the internal cavity of housing 201 while still allowing essentially unimpeded sound transmission into the cavity. This is a desirable element where moisture can compromise the efficacy of the transducer. Such a barrier might be constructed from a thin plastic film or a mesh that impedes moisture from entering but does not seal the cavity completely.

A further refinement of the invention relates to attachment of the diaphragm to the housing as shown in FIG. 19. The tension, stiffness or resonance of the diaphragm 202 affects the sound quality. Attachment means 209 can have a significant effect on the diaphragm tension and stiffness. In one embodiment of the invention, attachment means 209 includes a means to adjust diaphragm attachment stiffness and tension. In one embodiment of adjustable diaphragm tension, attachment means 209 has a curved or angular inner surface 209A which presses against the diaphragm and holds it against housing 201. Attachment means 209 is preferably a screw-on ring with threads between the ring and housing 201. As the attachment means 209 is tightened, the outer edges of the diaphragm 202 are pushed downwards towards the rim of housing 201. This produces slight flexing of the diaphragm 202. Such flexing increases diaphragm tension, stiffness and changes resonant frequency. Attachment means 209 thus provides control of diaphragm resonance by adjusting the force applied at the periphery of the diaphragm 202. This is simply one embodiment of diaphragm resonant frequency and tension control, and the invention includes any method by which a user can adjust the sound characteristics of the transducer by setting diaphragm stiffness and tension. This could be achieved by a stretching mechanism which applies forces perpendicular to the circumference of the diaphragm, or other mechanical means by which to exert force on the diaphragm to change its stiffness, tension and resonant properties.

Figure 20:
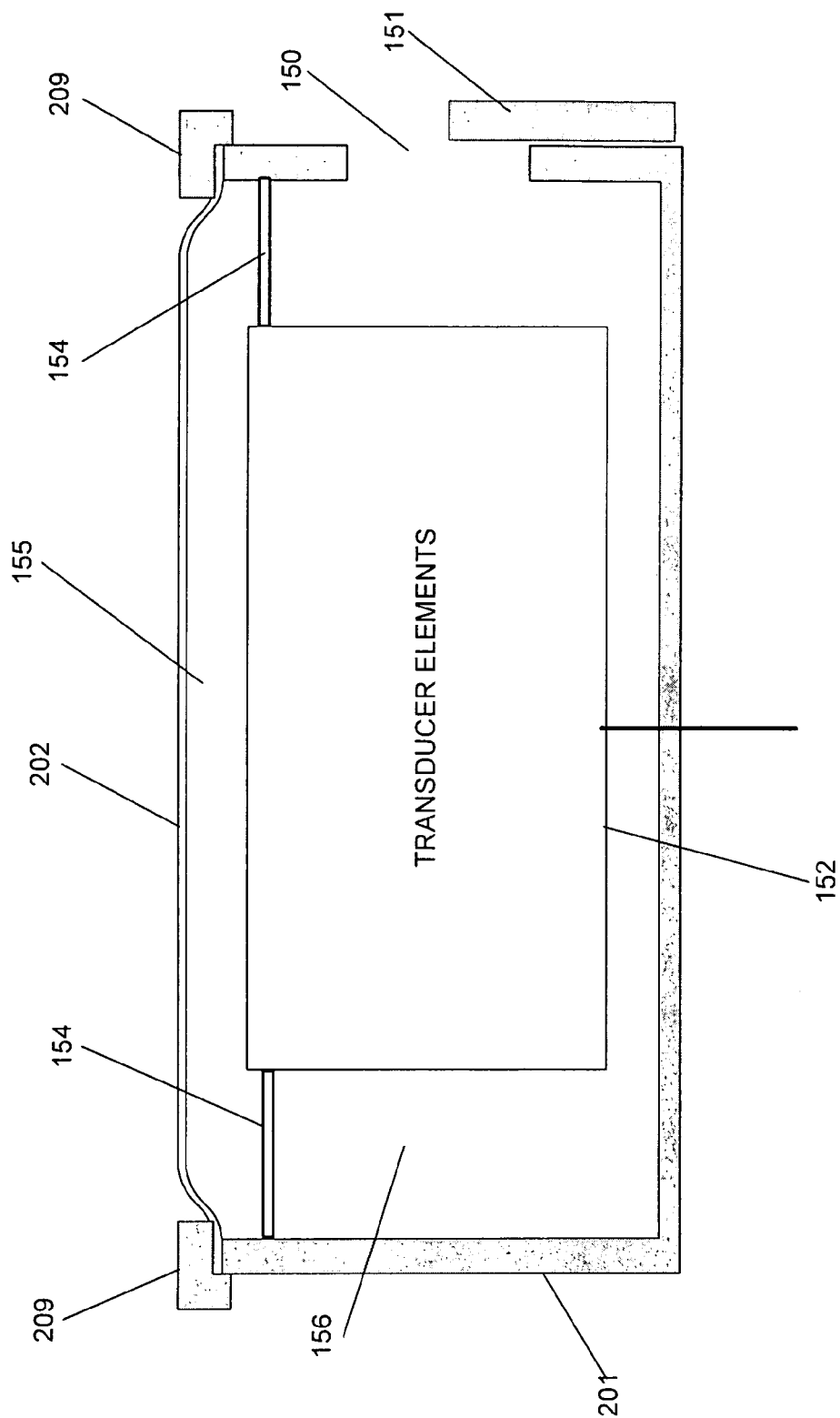
FIG. 20 shows a transducer housing with multiple cavities in which a small cavity behind the diaphragm is sealed to ambient sound while other cavity(ies) in the housing are open to external sound.

FIG. 20 shows a further refinement of an open housing in which a small space behind the diaphragm is closed by barrier 154, such that housing 201 has two or more internal cavities 155 and 156. In this case, cavity 155 behind the diaphragm 202 is of a small volume typically less than 1200 cubic millimeters, and in some cases smaller than 700 cubic millimeters when the space between diaphragm and transducer mechanism is sufficiently small. Barrier 154 can take two forms—a solid barrier that blocks sound transmission, and a very pliable thin barrier that blocks moisture and humidity but allows almost unimpeded transmission of sound. In the case where barrier 154 is solid, a small hole might optionally be added to equalize air pressure between cavities 155 and 156 while blocking sound transmission.

The principle of opening the transducer space behind the diaphragm can be extended more radically to allow for complete or almost complete mechanical separation between the diaphragm and the other elements of the transducer mechanism. In such an embodiment, the diaphragm is placed in physical contact with the body, and can optionally be adhered or attached to the body. The transducer is then placed in close proximity to the diaphragm but spaced from it such that diaphragm movement and vibration can be sensed even though the diaphragm is not physically coupled or attached to the transducer housing.

Figure 21:
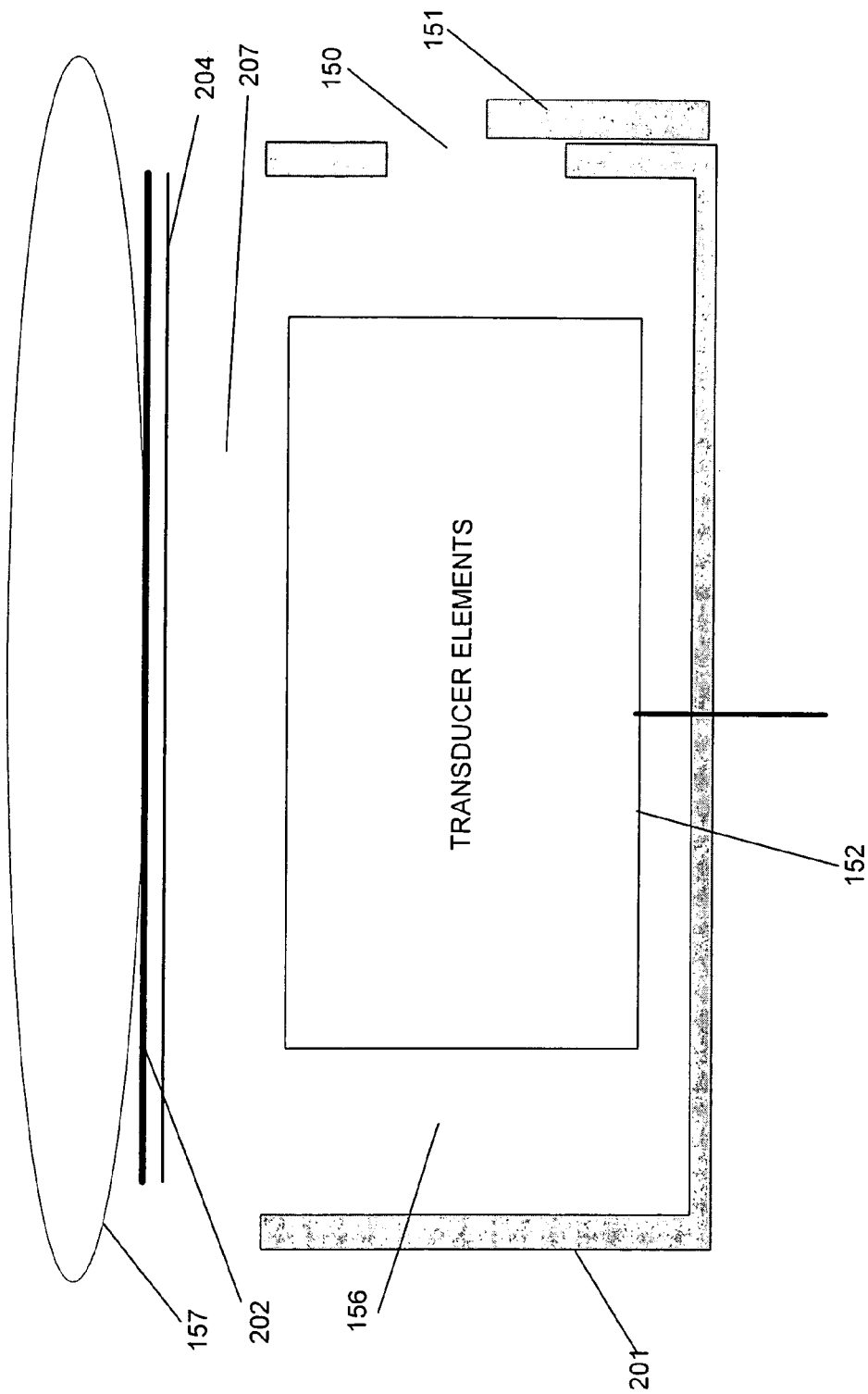
FIG. 21 shows a diaphragm that can be separated from the main transducer housing, and attached to a body.

This separation of the diaphragm from the housing is shown in FIG. 21. Diaphragm 202 is physically detached from or very loosely coupled to housing 201 which contains any of the transducers 152 described in this invention whether capacitive, magnetic or optical. The transducer method of operation is substantially the same as previously described, wherein the diaphragm is displaced by body sounds and the transducer senses this change in due to vibration. In this embodiment, diaphragm 202 may optionally be adhered with an adhesive material or otherwise attached to the body 157, and may optionally be flexible and take the shape of the body.

In the case of the capacitive transducer, diaphragm 202 includes a conductive plane 204 connected to a common circuit to provide a common reference potential between the conductive plane and the transducer so that conductive layer 204 forms a capacitor with the capacitive transducer plate. Diaphragm 202, having a conductive material 204 as part of its construction, can be used for both body sound detection and electrocardiogram (ECG) electrodes. A single conductive plane could be connected for body sound detection or ECG measurement. Alternatively conductive layer 204 could comprise two conductive layers insulated from each other, with one conductive layer acting as an ECG electrode against the body and the second electrode being the capacitive transducer electrode 204 facing the capacitive transducer.

In the case of the magnetic transducer embodiment, diaphragm 202 includes any of the magnetic elements that comprise the elements that are displaced by body sounds. In the case of an optical transducer, diaphragm 2 is reflective to facilitate optical detection of vibration. In either case, an ECG electrode can be incorporated into any diaphragm that is adhered to the body.

Note that in either the optical or capacitive embodiments of the invention, the diaphragm could be removed from any embodiment and the skin used as a reflective surface or electrode respectively. This is not considered a desirable embodiment of the invention and would be subject to skin conditions and other factors that would most likely result in less than ideal body sound detection means compared with the use of a diaphragm that has controlled properties.

Figure 22:
FIG. 22 shows a separate flexible diaphragm assembly that can be adhered or attached to a body.

Another embodiment of the capacitive transducer with detached flexible diaphragm is shown in FIG. 22. Diaphragm 202 and plate 203 are both detached from the housing to form a sandwich that is flexible and adhered or attached to the body 157 in such as manner that the plate and diaphragm form a capacitance for body sound sensing as described earlier in this invention. The capacitive space is ensured by a deformable substance or dielectric 205 such as foam or rubber placed in the inter-electrode space. The flexible capacitor includes means to connect the electrodes to the transducer electronics. While this is one embodiment of a flexible capacitive sensing means, the invention is intended to cover any flexible capacitive pad for sensing body sounds by detecting capacitance changes.

In all the above embodiments of the invention which include a detached diaphragm, both sound and air can pass between the diaphragm and other elements of the transducer thereby reducing standing waves or resonances that might otherwise be transduced in a closed cavity transducer. The housing 201 in such embodiments can also include apertures 150 to allow unimpeded sound transmission into the housing. These separable diaphragm embodiments can be applied in the detection of body sound vibration for both living bodies and inanimate objects, where in both cases, the diaphragm can be adhered or attached to the body, and the other parts of the transducer mechanism are fixed or held at a distance from the surface to which the diaphragm is attached.

Improvements to the present invention include various methods and structures for reducing the effects of ambient noise. A further means of rejecting ambient noise, beyond the apertures and diaphragm adjustment, is by various methods of adaptive or non-adaptive noise canceling and active noise control. Such methods require the addition of a second audio transducer, such as a microphone, that is configured to primarily detect ambient noise, and not the primary signal of interest, in this case body sounds. This is typically achieved by mounting the noise detection microphone so that it is coupled to the external atmosphere, not the internal cavity of the transducer housing. The reason in that most body sound detectors use microphones in the internal housing to detect body sounds, and a second microphone placed within the housing would simply duplicate the signal detection of the primary transducer. The present invention departs from this convention by allowing for the placement of a noise detection transducer within the transducer housing. However, in this invention, the transducing of diaphragm motion directly to an electrical signal means that the body sound transducer is far more effective at detecting body sounds than a microphone placed in the transducer housing cavity, such that a microphone placed within the cavity of the transducer housing would, relatively speaking, detect mostly ambient noise as it exists in the transducer housing. This is especially true in the case where the housing is open to ambient sound, and no pressure buildup occurs within the housing cavity. Another benefit of this internal cavity microphone is that the noise as detected by such a microphone is more closely matched to the ambient noise as detected by the body sound transducer since the cavity itself performs some noise-matched filtering. Subsequent noise canceling is thus more effective.

FIG. 19 shows noise-sensing transducer 160 placed within transducer housing 201, such that the noise transducer diaphragm 161 faces the cavity space. The output of this transducer is then available for use in ambient noise-canceling.

FIG. 18 shows a noise-canceling conductive diaphragm 162 added to the basic capacitive transducer structure. This becomes a second diaphragm capacitively coupled to plate 203. Diaphragm 162 is connected to a DC or ground reference in the same way was diaphragm 202. While diaphragm 202 is sensitive primarily to body sounds, diaphragm 162 is sensitive almost exclusively to ambient sound within the cavity of housing 201. Diaphragm 162 is weighted and tensioned such that its sensitivity to ambient noise is the same as that of diaphragm 202. As diaphragm 202 moves away from plate 203 due to ambient noise, diaphragm 162 moves towards plate 203, and vice versa through the vibrational cycles caused by ambient noise. Thus any voltage change in plate 203 produced by ambient noise on diaphragm 202 is countered by the inverse voltage change due to diaphragm 162. In an ideal case, ambient noise is completely nulled at plate 203 so the output of the capacitive transducer is noise-canceled prior to any signal processing. Physically diaphragm 162 can be stretched all the way across the inside of housing 201 to enclose a cavity behind diaphragm 202. Alternatively, diaphragm 162 can be smaller than plate 203. A third possibility is that plate 203 is mechanically separated into two plates, one capacitively coupled to diaphragm 202 and the second to diaphragm 162 thereby forming two capacitive sensors. Each plate can be charged by the same high voltage DC source, but be separately connected to two separate amplifier circuits or connected together to produce a single output. This offers the advantage that some of the electronics required to form a capacitive transducer can be shared by multiple capacitive transducers, each producing their own output signals for use in noise canceling.

In FIGS. 18 and 19, the noise canceling transducers are shown for the general case of a housing that can be opened or closed. This invention covers internal cavity-located noise transducers for fully closed housings that do not have apertures, housings with apertures, or those with adjustable aperture openings.

Figure 23:
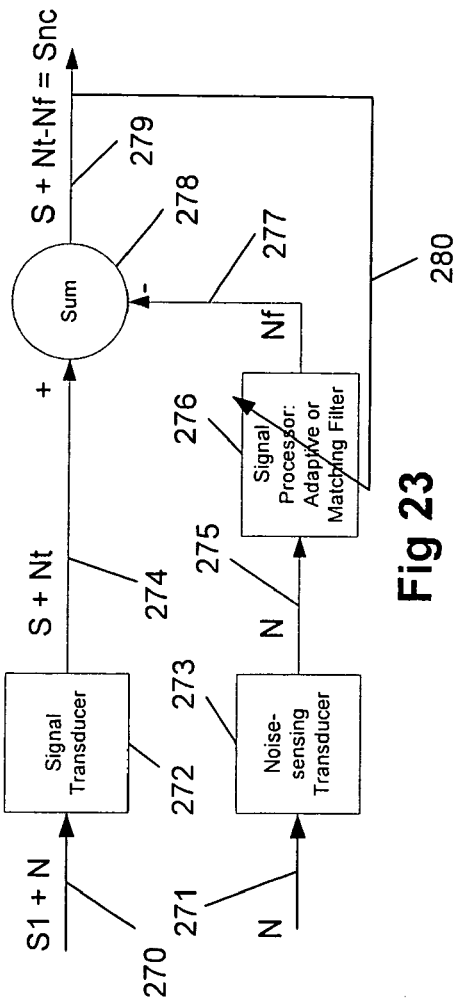
FIG. 23 shows the conventional topology of a noise-canceling system.

Noise canceling using such noise-sensing transducers can be performed by techniques that are well known in the art as shown in FIG. 23. Transducer 272 receives signal (S1) plus noise (N) and outputs S+Nt, where S is the transduced signal and Nt is the noise as converted by signal transducer 272. Nt is preferably an attenuated and filtered version of N, since transducer 272 is usually designed to transduce S better than N. A noise-sensing transducer 273 receives noise N, and usually little or no Signal S. Filter 276 filters signal 275 (N) to output Nf, which is preferably almost identical to Nt. The summing function 278 performs S+Nt−Nf to produce noise-canceled signal Snc which is equal to S if Nt=Nf. In a real system, Nf is not necessarily equal to Nt, especially if filter 276 is not well-matched, and Snc contains some remnants of noise N. An improved implementation includes feedback of the output 278 via feedback signal 280 to adjust filter 276 so that Nf=Nt. This adaptive noise canceling is well-known and effective for certain classes of noise signals. Such adaptive filter topologies as shown in FIG. 23 have been proposed in the prior art for use in body sound sensors and stethoscopes.

Figure 24:
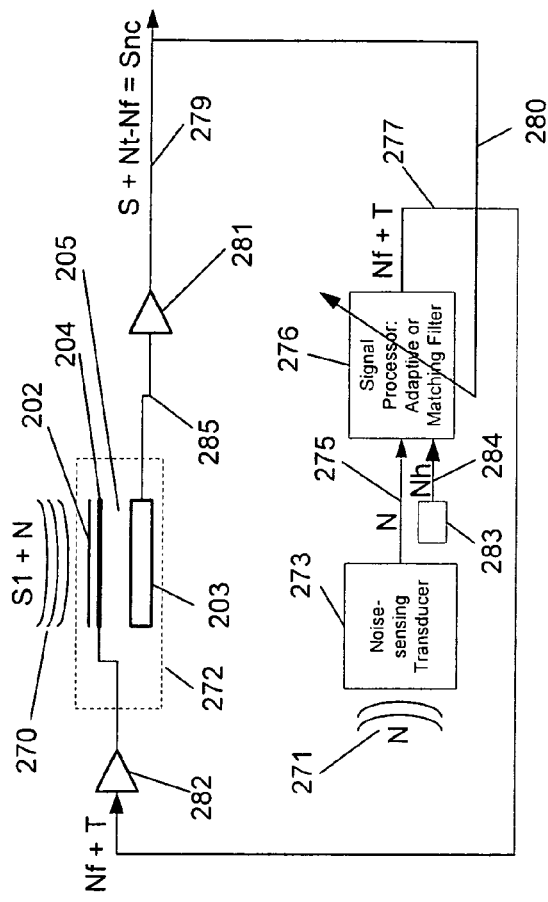
FIG. 24 shows the topology and details of a noise canceling capacitive transducer.

The present invention provides a novel topology for implementing noise canceling wherein a capacitive signal transducer is driven with both mechanical/acoustic input and an electrical noise-canceling signal. This is shown in FIG. 24. Signal transducer 272 is a capacitive transducer with diaphragm 202 displaced by acoustic or mechanical energy (S1+N) 270. Conductive plane 204 which is part of diaphragm 202 forms a capacitance with plate 203. A high impedance voltage signal 285 is buffered by high impedance buffer amplifier 281 to provide the transducer output signal 279. Noise-sensing transducer 273 transduces acoustic noise signal N 271 to filter/signal processor 276. Filter 276 produces filtered noise signal (−Nf, if T=0) 277 which is fed back via low impedance driver 282 to capacitive transducer 272 to cancel noise N as mechanically transduced by the diaphragm of transducer 272. The result is that the output 279 of transducer 272 is a noise-reduced or noise-canceled signal Snc. Thus instead of the signal processing topology using two transducer signals to produce a third noise-reduced signal by subtraction, this topology uses two transducer signals to produce a noise signal which is fed back to the transducer itself so that the transducer signal output is noise-reduced. This is a novel method compared with the conventional method. Advantages include the ability to cancel noise before it saturates buffer amplifier 281, and being able to pass transducer signal 279 downstream without further processing. Further, filter/processor 276 can be implemented in analog or digital circuitry while the signal path from transducer 272 could be entirely analog to maintain signal resolution.

The filter 276 can be fixed, adjustable or adaptive. A fixed version implements a transfer function that is matched to the noise transfer function of the transducer 272. An adjustable version provides a means for the user to manually adjust the filter to aurally null ambient noise. An adaptive filter implementation uses signal 280, the output of transducer 272 to adaptively adjust filter parameters to null ambient noise. This is the preferred embodiment, since it provides the best signal to noise ratio.

In an expanded embodiment of the filter with feedback, filter 276 performs further signal generation and processing functionality. Specifically, signal processor/filter 276 generates a tracking signal T which is injected into capacitive transducer 272 and tracked via the output 279 and feedback signal 280. The tracking signal is then filtered out of the transducer signal in a downstream filter. The tracking signal is used to track the static or dynamic displacement of the diaphragm. For example, a sinusoid fed into capacitive sensor would be amplitude-modulated by the displacement of the diaphragm. The signal processor 276 then uses this information to perform one or more of the following functions: (a) adjust filtering parameters for noise canceling, (b) change filtering parameters and feed these changes to a signal filter, such as changing the "bell" or "diaphragm" mode filtering parameters or to create a smart pressure-sensing tone control function (c) detect whether the diaphragm is being displaced by a body or is exposed to free air and perform switching or mode functions accordingly, such as muting the noise canceling signal or powering down a system for power saving.

The capacitive transducer of FIG. 24 can be made "intelligent" with respect to potential noise sources. Filter/Processor 276 could be programmed to detect certain known noise signals and generate anti-noise signals that specifically target certain signature disturbances. These might be such signals as overload impulses, power line hum, well-correlated periodic signals such as the vibration of a helicopter engine, or other signature signals. This gives the capacitive transducer unique intelligence to null certain predicted mechanical disturbances before they are able to saturate the buffer amplifier 281.

The methods shown in FIG. 24 apply to capacitive transducers in general, but are particularly useful for capacitive acoustic sensors, and especially in the application of capacitive sensors to body sound detection, where ambient noise is a significant problem. Stethoscopes in particular can benefit from this noise cancellation technique due to the low amplitude of body sound signals in the presence of high ambient noise. A slight modification can be made to the configuration shown in FIG. 24 wherein the noise canceling signal is coupled to plate 203 instead of to conductive plane 204 as shown. This invention includes all configurations in which a noise-canceling signal is driven into the capacitive electrodes of a capacitive transducer.

A further improvement in noise reduction can be achieved by canceling noise that enters the headphone cavities. A headphone noise-sensing microphone 283 feeds headphone noise signal Nh 284 into filter/processor 276 which incorporates this into the construction of anti-noise signal Nf to be driven into conductive plane 204. This is once again a departure from the conventional noise-canceling method in that the transducer signal is corrupted by headphone noise, in order to correct the perceived sound. Alternatively, a noise-canceling feedback loop downstream from the transducer output can perform noise canceling to compensate only the noise that leaks into the headphones, while the processor 276 only corrects the transducer-detected noise.

In the above description, the processor and signals may take the form of analog circuitry, digital signal processors with analog-to-digital and digital-to-analog conversion, or combinations of the two signal processing methods. A particularly cost-effective and low-noise solution might take the form of an analog forward path from the plate 203 all the way to the headphones or other outputs, and a digital processor 276 with digital-to-analog conversion to drive the diaphragm plane 204. This has the benefit that the actual transducer output does not required analog-to-digital conversion, allowing for the greater dynamic range of a purely analog system where no quantization occurs. This invention includes all such combinations of analog or digital implementations.

A particularly cost-effective noise-canceling embodiment could be implemented by a completely analog solution, in which the feedback processing 276 is tuned manually by the user. In this scenario, the user would listen to the resulting signal, perhaps in the presence of ambient white noise, and adjust the amplitude and frequency response of processing function 276 until the optimal sound is heard. This would obviate the need for sophisticated signal processing that would automatically tune the feedback noise signal 277.

Figure 25:
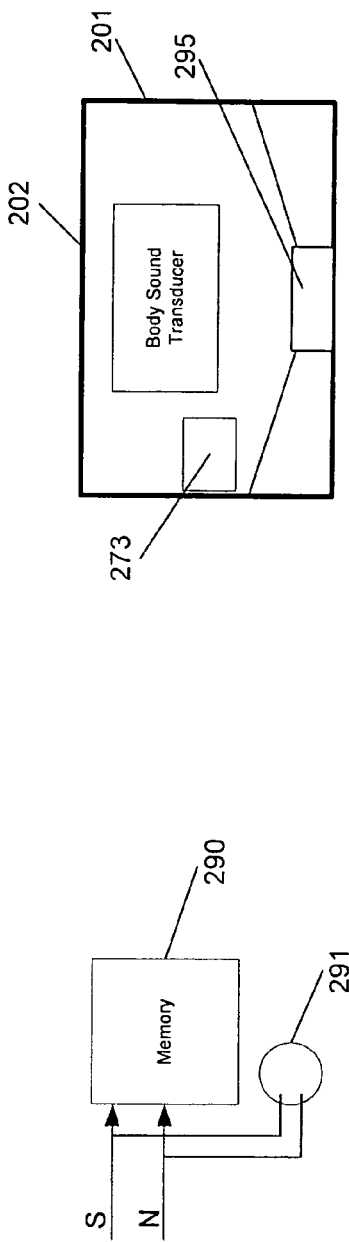
FIG. 25 shows the storage and transmission of both signal and noise for further processing.

Extending the goal of a low-cost embodiment of a noise-canceling system, FIG. 25 shows an embodiment which includes an output port with both the transducer signal, or filtered version thereof, and noise transducer 273 output signal 275. In this embodiment, an external signal processing system can provide the noise reduction function. This provides for the ability to connect the transducers described in this invention to a powerful signal processor for noise reduction. Such an embodiment can be applied to capacitive, magnetic, optical or any other body sound transducer system. The embodiment also allows for both noise signal 275 and primary transducer signal 279 to be stored in memory 290 for post-processing or archiving. This allows noise reduction to be implemented later, even using algorithms that are unknown at the time of recording and storage.

Figure 26:
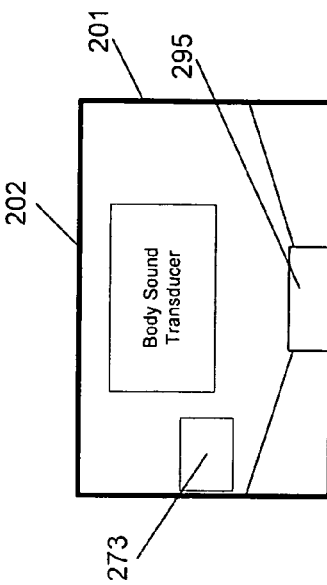
FIG. 26 shows an active noise canceling method wherein a speaker mounted in the transducer housing produces antinoise in order to reduce the noise level inside the transducer housing.

FIG. 26 shows a noise reduction system that includes a speaker 295 in the transducer housing 201 wherein the speaker is driven with an anti-noise signal to reduce the noise as transduced by diaphragm 202. This method is applicable to all transducers disclosed in this invention. The housing 201 could have aperture(s) to the ambient atmosphere or be closed. Noise detector 240 is optionally included in this embodiment to provide a feedback signal for noise cancellation. The primary benefit of this system is that it can be implemented with any transducer, whereas some of the above noise-canceling schemes apply only to the capacitive transducer.

The principle of driving the diaphragm conductive plane with a varying electrical signal, as an alternative signal input to the transducer provides some very novel methods for signal input into the capacitive body sound detector providing a dual-use transducer that can sense either body sounds or electric fields with only minor modifications. Consider the embodiment shown in FIG. 27. Housing 201 contains the capacitive transducer in this invention, except that the conductive diaphragm has been removed from the housing, optionally replaced by a non-conductive diaphragm 302 which acts merely as a cover. The capacitive transducer now no longer has a first electrode to form a variable capacitance for mechanical vibration detection. It also does not have the shielding provided by the conductive diaphragm. Audio signal source 300 outputs an audio signal Asig via an optional driver circuit to drive an Asig voltage into electrode 304 which is not mounted or attached to housing 201, but is attached to some other body 321. Signal source 300 is connected to the same ground reference point 299 as the transducer circuitry. The voltage signal Asig on electrode 304 is capacitively coupled to plate 203 and output 279 by the transducer. The electrical signal Asig is technically indistinguishable from a signal produced by voltage changes on plate 203 caused by displacement of a conductive diaphragm. A voltage on electrode 304 therefore simulates the motion of a diaphragm due to mechanical displacement. Note that Asig can comprise any audio or other waveform.

Figure 28:
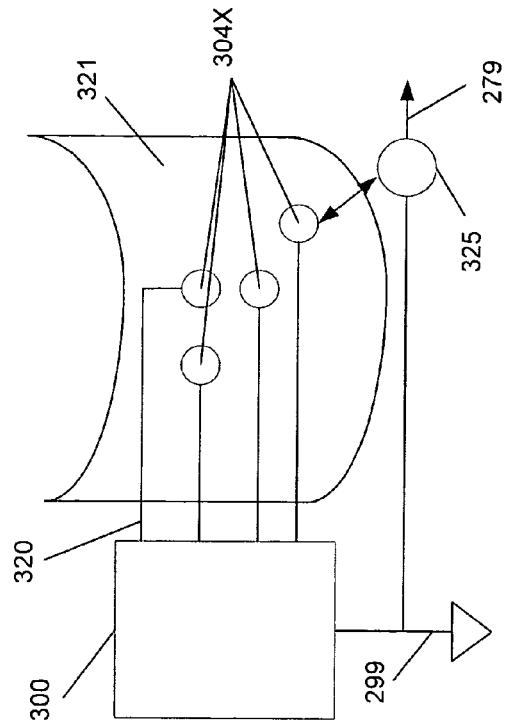
FIG. 28 shows modifications of the diaphragm in connection with use of an external electrode.
Figure 29:
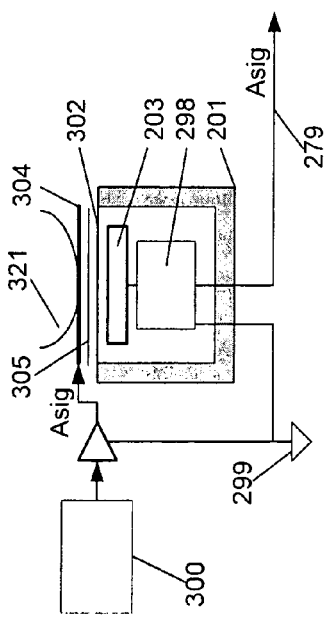
FIG. 29 shows modifications of the transducer to provide flexibility in the application of the capacitive transducer for voltage and biopotential detection, and for use with external electrodes for simulation.

FIGS. 28 and 29 show various modifications that facilitate convenient interchange between acoustic sensing and electric field sensing, making only minor modifications to the capacitive transducer, such that a user can make such changes conveniently and quickly.

In FIG. 28, the conductive diaphragm is replaced by a non-conductive or partially conductive diaphragm 302. FIG. 28 schematically shows a number of possible embodiments of diaphragm 302: (a) The diaphragm has a hole that allows an external electrode 304 to protrude through the diaphragm to make conductive contact or close capacitive connection with plate 203. (b) Diaphragm 302 has a conductive plane over much of its surface for shielding plate 203, but has an area that is non-conductive, so that the voltage change on electrode 302 can be detected by plate 203.

FIG. 29 shows a modification of the capacitive transducer wherein an adapter is placed on the housing 201. The adapter comprises a second plate 203A and attachment housing 201A. The second plate optionally has additional height or a protrusion to facilitate capacitive or electrical contact between plate 203 and external electrodes. This provides a connection for use of the transducer plate 203 for sensing biopotentials. If conductive contact is undesirable, dielectric 205A is optionally placed over plate 203A. FIG. 29 also shows a connector means 211, which provides for a plug and cable to be connected to plate 203 and housing 201. Such an arrangement provides connection of the capacitive sensor to any arbitrary external sensing device.

Figure 30:
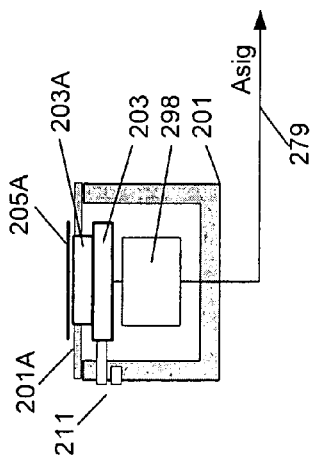
FIG. 30 shows a multi-electrode system, such as could be used on a minikin, to be used in connection with a capacitive transducer.

The electrically-driven capacitive transducer can be applied as shown in FIG. 30.

Figure 27:
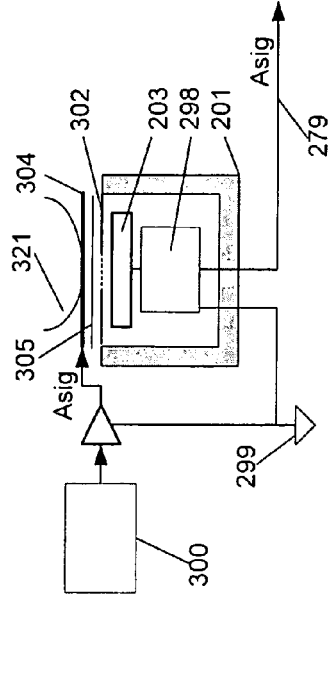
FIG. 27 shows an externally-driven electrode arrangement for the capacitive coupling of signals into the capacitive transducer.

Signal source 300 has one or more drive signals 320 which are connected to one or more electrodes 304X placed on a body 321. If the capacitive transducer without conductive diaphragm, as shown in FIG. 27, is then placed in close proximity to an electrode 304X, the transducer will detect the electrical signal being driven by source 300 and convert it to an electrical signal that can be made indistinguishable from a signal produced by a conductive diaphragm being displaced by an acoustic or mechanical source. The body 321 can be a real human or animal body, a model of a human body such as a manikin, a garment to be worn by a person or placed on a model, a toy or doll, or any other inanimate object. The embodiment shown in FIG. 30 thus provides for the electrical drive of one or more electrodes attached or mounted on any object, the purpose being that the voltages on these electrodes be detectable by the capacitive transducer for the purposes of simulating the detection of an audio signal by the capacitive sensor. The present invention thus provides the novel embodiment of a vibration simulator wherein electric fields replace mechanical vibration and a capacitive transducer is modified to sense such electric fields.

The electrodes 304X are preferably round in shape, and when used for capacitive coupling, have a surface area at least 300 square millimeters although smaller areas can work if the drive signals to the electrodes are sufficiently large to be detected by a capacitive detector.

A further extension of the embodiment shown in FIG. 30 provides for signal source 300 to drive biopotential signals such as ECG, EMG, or EEG to such electrodes placed on an object or manikin for the purposes of simulating electrical physiological phenomena. In such a case, the capacitive transducer might ideally be adapted so that conductive diaphragm is removed, and the capacitive plate sensor 203 can be brought into electrical contact with the external electrodes 304X to make a direct connection to the simulation signal source. This inventive step provides a dual-use capacitive transducer wherein the electronics normally used for capacitive acoustic sensing in connection with a movable conductive diaphragm can also be used for measuring biopotentials. The advantage of this method is that both the capacitive sensing electronics and biopotential sensing electronics require a differential voltage measurement with a very high input impedance, so dual use is possible. This is unique in that the prior art requires acoustic phenomena to be simulated by mechanical means, and this invention includes means for using non-moving means to simulate acoustic energy.

The embodiment shown in FIG. 30 can be applied to a medical training system, wherein electrodes are placed on a manikin at typical listening sites used in clinical practice for listening to heart, lung, bowel or other body sounds. Signal source 300 then drives each electrode with a body sound signal appropriate to that site. Medical students or others can then place their stethoscopes at these electrode sites, and listen at each site to what would be expected to be heard at that site. Signal source 300 could contain a database of signals for various pathologies and drive them to each location to provide a life-like physical examination experience for medical students or others. In another embodiment, electrodes can be placed on a garment such as a body stocking, tank top, T-shirt, etc. and the garment could then be worn by a subject. Once again, signal source 300 drives sound appropriate to each site for an given pathology. This allows medical students to listen to sounds on a human or manikin and gain experience listening to such sounds as if they were being generated by the body sounds of a patient with a given pathology. This could provide more education and training than is possible in a real-life situation, since the recordings can contain pathologies that are too rare to encounter in regular medical training or practice.

The electrodes 304X in FIG. 30 can also be fabricated with adhesive backing and electrical connections 320 such that they can be adhered individually to an object or human body. This embodiment allows medical students, nurses and others to apply the electrodes on the body for training, then make the electrical connection 321 between said adhesive electrodes 304X to signal source 300, and then use the capacitive transducer to simulate listening to various pathological signals on live human subjects.

The signal source 300 can take various forms including but not limited to: (a) a custom signal source, (b) personal computer sound output (c) handheld computer audio output (d) CD player, (e) MP3 player, (f) wired or wireless network-connected computer system (g) internet-connected computer system. Thus any audio signal source such as those described could be connected via their standard line or headphone drive outputs, to electrodes placed on a body, and the capacitive transducer placed in close proximity to the electrodes, such that the audio signals can be detected by the capacitive transducer and heard by a user. Alternatively, the signal source 300 can take the form of a digital signal generator, wherein the digital signal identifies the electrode. Such a system could then be used in an educational system to communicate the position of a sensing device such as a stethoscope on an object such as a manikin. The position could then be used to trigger certain audio signals that are not necessarily being transmitted via the electrodes, but are communicated via other means to the listener, the particular channel being a function of the digital code at that particular electrode.

The setup in FIG. 30 also provides the facility for students to study or take tests. The signal source 300 can be a computer with user input and display allowing the user to listen to the sounds via the capacitive transducer, perhaps in the form of a stethoscope, and respond to questions related to the sounds via the user interface means for learning or student examination purposes. This system provides for the teaching and examination of auscultation skills, which has become exceedingly difficult within the time and budget constraints of medical education. If the physical placement aspects of the sounds are not required to be implemented on a model or manikin, the system shown in FIG. 30 can be modified by dispensing with the electrodes and transmitting the sounds via an electrical or wireless connection directly to the stethoscope, using the stethoscope headphones to provide a realistic reproduction of sound to the listener. In other respects, the testing and education system could remain the same as shown in FIG. 30, except for the absence of the physical or spatial implementation made possible by the electrode placement on a physical body. This system has application not only for medical students, but for nursing, EMT and other paramedical personnel, as well as training caregivers such as parents with asthmatic children who must learn to differentiate various pulmonary conditions.

It should further be noted that the signals transmitted to the electrodes need not be limited to body sounds, but could include other audio signals of interest or value to the listener. In a medical setting, this could include instructional information including voice and music to provide annotation and explanation to the listener, along with body sound recordings. A further medical application could comprise the steps of recording body sounds from a patient using an electronic stethoscope, annotating the positions on the body at which the recordings were made, assembling the sound recordings and annotations into a data file, and transmitting or recording the compiled record. The stored data can then be made available via transmission or on the internet to others such as at remote locations, who could download said data file and reproduce the body sounds, at the sites from which they were recorded, using the electrodes 304X at the respective sites on the body or manikin 321. This allows any stethoscope user to compile case studies with auscultatory findings and share them with others for education or consultation.

The invention shown generically in FIG. 30 also includes the implementation of the electrode reproduction system for use in entertainment and recreation. In this application, signals are transmitted from a signal source 300 to a human or inanimate body. The capacitive transducer is then placed in close proximity to the electrodes, so that the voltage signals at the electrodes are detected by the capacitive transducer to be reproduced such as in the headphones of a stethoscope, or transmitted for reproduction via a loudspeaker. This general-purpose embodiment can be applied to toys, wherein the electrodes are placed on a doll, and a child can play at examining the doll's bodily sounds, such as breathing and heartbeat, and even simulate taking a blood pressure or detecting a fetal heartbeat in a "pregnant" doll. Thus dolls could be imbued with simulated bodily functions for educational and recreational use.

In an entertainment setting, dancers or actors could wear the body stocking with electrodes or apply adhesive electrodes with signal sources driving the electrodes, and then use a capacitive transducer to selectively place and transfer different sounds into the transducer as a function of position. The sounds can then be transferred to an audio amplifier and loudspeaker system. This activity could be performed on a choreographed basis whereby body position and electrode position can be used to control music or general sound. By modifying the signals sent to the electrodes by signal source 300 in such a scenario, an infinite variety of sound sequences and associated body movements would be possible.

This invention includes capacitive, magnetic and optical body sound transducers. The method of applying electrodes to human or inanimate bodies and using the body sound transducers adapted for use to detect artificial body sounds can be extended beyond the capacitive implementation described above. In the case of magnetic sensors, the external electrodes 304X could be replaced in the above description with magnetic field transducers that produce magnetic fields at various sites on a body. Similarly, the optical transducer could be used in conjunction with optical output devices such as LEDs placed on a body. In this case, the optical transducer is placed on the body over such light emitting devices and depending on the site and stimulus to such optical output devices, the optical sensing transducer could receive different stimuli based on physical position. With current technology, the capacitive transducer method described herein is the most cost-effective and therefore the most preferred embodiment. However this invention covers the combination of artificial signal sources and body sound transducers of all three methods—capacitive, magnetic and optical. The overall uniqueness of the invention in this regard is that a non-mechanical, non-acoustic energy source is placed on a body to simulate sounds at various physical locations, and the body sound transducers are minimally modified to receive such stimuli, thereby simulating body sounds via non-mechanical detection, with almost all elements of the body sound transducer remaining in place and used as if the stimulus were mechanical. As stated earlier, the capacitive transducer requires modification merely in the replacement of the conductive diaphragm with a non-conductive diaphragm or by complete removal of the diaphragm, so that the capacitive plate already in place can be capacitively coupled to external electrodes. Thus a modification that can be performed by the user in a matter of seconds transforms the body sound transducer to an electric field transducer but in all other respects, the use of the device is the same as if mechanical vibration were being measured. This is a unique combination and as indicated in the above discussion, offers myriad possibilities in education and even entertainment.

The invention claimed is:

1. A stethoscope with acoustic-to-electrical transducer for detecting body sounds, the transducer comprising:
   a diaphragm mounted in a housing such that the diaphragm can make contact with a body and vibrate in response to body sounds; a diaphragm displacement-to-electrical conversion means to convert diaphragm displacement due to body sound vibrations to electrical signals; and
   the transducer housing having one or more apertures or openings to provide a low-impedance acoustic path for ambient sound to enter the space within the housing including the space behind diaphragm.

2. The transducer according to claim 1, wherein the apertures can be opened or closed by a user.

3. The transducer according to claim 1, further comprising a moisture barrier with low acoustic impedance placed between the apertures and the internal housing cavity, such that a low impedance acoustic path for ambient sound to enter the housing cavity is maintained, while moisture and humidity are prevented from entering the cavity.

* * * * *